(12) United States Patent
Yabunouchi et al.

(10) Patent No.: US 7,976,957 B2
(45) Date of Patent: Jul. 12, 2011

(54) AROMATIC AMINE DERIVATIVE AND ORGANIC ELECTROLUMINESCENT ELEMENT EMPLOYING THE SAME

(75) Inventors: Nobuhiro Yabunouchi, Chiba (JP); Hisayuki Kawamura, Chiba (JP); Chishio Hosokawa, Chiba (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 864 days.

(21) Appl. No.: 11/909,725

(22) PCT Filed: Mar. 2, 2006

(86) PCT No.: PCT/JP2006/303980
§ 371 (c)(1),
(2), (4) Date: Sep. 26, 2007

(87) PCT Pub. No.: WO2006/112166
PCT Pub. Date: Oct. 26, 2006

(65) Prior Publication Data
US 2010/0141119 A1 Jun. 10, 2010

(30) Foreign Application Priority Data

Mar. 30, 2005 (JP) .................................. 2005-097786

(51) Int. Cl.
*H01J 1/63* (2006.01)

(52) U.S. Cl. .......................... 428/690; 313/504; 564/434
(58) Field of Classification Search ........................ None
See application file for complete search history.

(56) References Cited

U.S. PATENT DOCUMENTS 6,632,543 B1 * 10/2003 Kawamura .................... 428/690
2007/0167654 A1 7/2007 Yabunouchi et al.

FOREIGN PATENT DOCUMENTS

WO 01/23344 4/2001

OTHER PUBLICATIONS

U.S. Appl. No. 11/855,556, filed Sep. 14, 2007, Yabunouchi, et al.

* cited by examiner

*Primary Examiner* — D. Lawrence Tarazano
*Assistant Examiner* — Gregory Clark
(74) *Attorney, Agent, or Firm* — Oblon, Spivak, McClelland, Maier & Neustadt, L.L.P.

(57) ABSTRACT

An aromatic amine derivative having a specific structure having m-terphenyl group and an organic electroluminescence device comprising a cathode, an anode and an organic thin film layer which is disposed between the cathode and the anode and comprises at least one layer comprising at least a light emitting layer, wherein at least one layer in the organic thin film layer comprises the aromatic amine derivative singly or as a component of a mixture. The organic electroluminescence device has a long life.

16 Claims, No Drawings

AROMATIC AMINE DERIVATIVE AND ORGANIC ELECTROLUMINESCENT ELEMENT EMPLOYING THE SAME

TECHNICAL FIELD

The present invention relates to an aromatic amine derivative and an electroluminescent element ("electroluminescent" and "electro-luminescence" will be occasionally referred to as "EL", and "electro-luminescent element" and "electroluminescence device" will be occasionally referred to as "EL device", hereinafter) employing the same, and more particularly to an EL device having a long life in combination with a sustained great efficiency of light emission and an aromatic amine derivative providing the EL device.

BACKGROUND ART

An organic EL device is a spontaneous light emitting device which utilizes the principle that a fluorescent substance emits light by energy of recombination of holes injected from an anode and electrons injected from a cathode when an electric field is applied. Since an organic EL device of the laminate type driven under a low electric voltage was reported by C. W. Tang of Eastman Kodak Company (C. W. Tang and S. A. Vanslyke, Applied Physics Letters, Volume 51, Pages 913, 1987), many studies have been conducted on organic EL devices using organic materials as the constituting materials. Tang et al. used a laminate structure using tris(8-hydroxyquinolinol)aluminum for the light emitting layer and a triphenyldiamine derivative for the hole transporting layer. Advantages of the laminate structure are that the efficiency of hole injection into the light emitting layer can be increased, that the efficiency of forming excited particles which are formed by blocking and recombining electrons injected from the cathode can be increased, and that excited particles formed within the light emitting layer can be enclosed. As the structure of the organic EL device, a two-layered structure having a hole transporting (injecting) layer and an electron transporting and light emitting layer and a three-layered structure having a hole transporting (injecting) layer, a light emitting layer and an electron transporting (injecting) layer are well known. To increase the efficiency of recombination of injected holes and electrons in the devices of the laminate type, the structure of the device and the process for forming the device have been studied.

In general, when an organic EL device is driven or stored in an environment of a high temperature and a high humidity, adverse effects such as a change in the emitted color, a decrease in the efficiency of light emission, an increase in the voltage for driving and a decrease in the life of light emission arise. To prevent the adverse effects, it has been necessary that the glass transition temperature (Tg) of the hole transporting material be elevated. For this purpose, it is necessary that the hole transporting material have many aromatic groups in the molecule (for example, aromatic diamine derivatives described in Patent Reference 1 and aromatic condensed ring diamine derivatives described in Patent Reference 2) and, in general, compounds having a structure having 8 to 12 benzene rings have been preferably used.

However, when many aromatic groups are present in the molecule, crystallization tends to take place during the formation of a thin layer using the hole transporting material in the preparation of an organic EL device, and the crystallization causes problems in that the outlet of a crucible used for the vapor deposition is clogged and that defects caused by the crystallization are formed in the thin layer, and the yield in the production of the organic EL device decreases. The compound having many aromatic groups in the molecule causes a short life, in general, since the compound has a high temperature of sublimation and problems such as decomposition of the compound during the vapor deposition and uneven vapor deposition arise although the compound has a high glass transition temperature (Tg).

Asymmetric aromatic amines are disclosed in references. For example, an aromatic amine derivative having an asymmetric structure is described in Patent Reference 3. However, no specific examples are described, and characteristics of the asymmetric compound are not described at all. An asymmetric aromatic amine derivative having phenanthrene is described in Patent Reference 4. However, the asymmetric compound is treated in the same manner as symmetric compounds, and characteristics of the asymmetric compound are not described at all. The synthesis of an asymmetric compound requires a special synthetic process. No processes for synthesis of the asymmetric compounds are clearly described in the above Patent References. A process for producing an aromatic amine derivative having an asymmetric structure is described in Patent Reference 5. However, characteristics of the asymmetric compound are not described at all. A thermally stable asymmetric compound having a high glass transition temperature is described in Patent Reference 6. However, the compounds described as the example are limited to compounds having carbazole. When a device using this compound was prepared by the present inventors, a problem was found in that the device had a short life.

As described above, although organic EL devices having a long life have been reported, no devices had a sufficient life. Therefore, an organic EL device having more excellent properties has been strongly desired.

[Patent Reference 1] Specification of U.S. Pat. No. 4,720,432
[Patent Reference 2] Specification of U.S. Pat. No. 5,061,569
[Patent Reference 3] Japanese Patent Application Laid-Open No. Heisei 8(1996)-48656
[Patent Reference 4] Japanese Patent Application Laid-Open No. Heisei 11(1999)-135261
[Patent Reference 5] Japanese Patent Application Laid-Open No. 2003-171366
[Patent Reference 6] Specification of U.S. Pat. No. 6,242,115

DISCLOSURE OF THE INVENTION

The present invention has been made to overcome the above problems and has an object of providing an organic EL device having a long life and an aromatic amine derivative providing the device.

As the result of intensive studies by the present invention to achieve the above object, it was found that the object could be achieved by using an aromatic amine derivative having a specific structure having m-terphenyl group represented by the following general formula (1) as the material for an organic EL device, in particular, as the hole transporting material. The present invention has been completed based on the knowledge.

It was also found that amino group substituted with m-terphenyl group had small interaction between molecules due to the great steric hindrance, and crystallization was suppressed. Therefore, the yield in producing the organic EL device could be increased, and the effect of increasing the life of the obtained organic EL device could be exhibited. In particular, the effect of a remarkable increase in the life could be exhibited in the combination with a device emitting bluish light.

The present invention provides an aromatic amine derivative represented by following general formula (1):

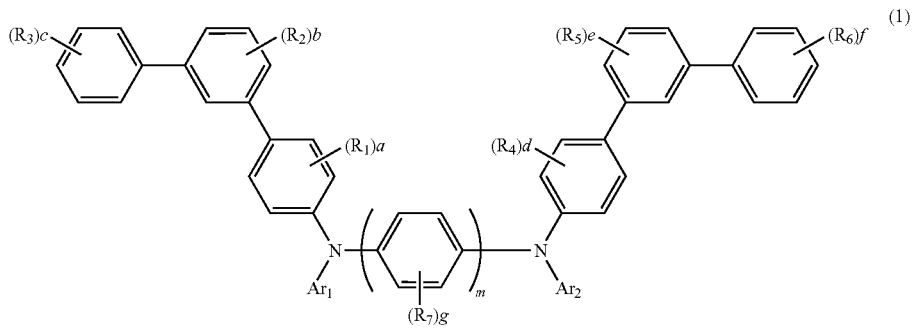

wherein $R_1$ to $R_6$ each independently represent a substituted or unsubstituted alkyl group having 1 to 10 carbon atoms, a substituted or unsubstituted alkoxyl group having 1 to 10 carbon atoms or a substituted or unsubstituted phenyl group, $R_7$ represents a substituted or unsubstituted alkyl group having 1 to 10 carbon atoms or a substituted or unsubstituted alkoxyl group having 1 to 10 carbon atoms, a, b, d, e and g each represent an integer of 0 to 4, c and f each represent an integer of 0 to 5, and m represents an integer of 1 to 3; and $Ar_1$ and $Ar_2$ each represent a group represented by following general formula (2), (3) or (4);

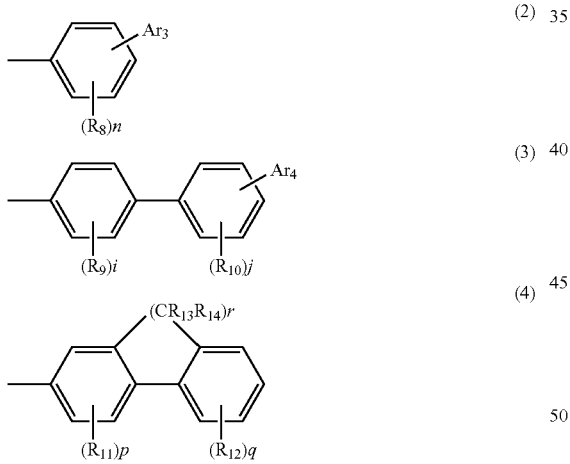

in general formula (2), $R_8$ representing a substituted or unsubstituted alkyl group having 1 to 10 carbon atoms, a substituted or unsubstituted alkoxyl group having 1 to 10 carbon atoms or a substituted or unsubstituted phenyl group, $Ar_3$ representing a substituted or unsubstituted phenyl group, a substituted or unsubstituted α-naphthyl group, a substituted or unsubstituted β-naphthyl group or a substituted or unsubstituted ortho-(o-), meta-(m-) or para-(p-)biphenyl group, bonding position of the group represented by $Ar_3$ being o- or m-position, and n representing an integer of 0 to 4;

in general formula (3), $R_9$ and $R_{10}$ each independently representing a substituted or unsubstituted alkyl group having 1 to 10 carbon atoms, a substituted or unsubstituted alkoxyl group having 1 to 10 carbon atoms or a substituted or unsubstituted phenyl group, $Ar_4$ representing a substituted or unsubstituted phenyl group, bonding position of the group represented by $Ar_4$ being o- or p-position, and i and j each representing an integer of 0 to 4; and in general formula (4), $R_{11}$ and $R_{12}$ each independently representing a substituted or unsubstituted alkyl group having 1 to 10 carbon atoms, a substituted or unsubstituted alkoxyl group having 1 to 10 carbon atoms or a substituted or unsubstituted phenyl group, p representing an integer of 0 to 3, q representing an integer of 0 to 4, $R_{13}$ and $R_{14}$ each independently representing single bond, hydrogen atom, a substituted or unsubstituted alkyl group having 1 to 6 carbon atoms or a group represented by following general formula (5), and r representing an integer of 1 or 2;

$$-(CR_{15}R_{16})_s- \qquad (5)$$

in general formula (5), $R_{15}$ and $R_{16}$ each independently representing hydrogen atom or a substituted or unsubstituted alkyl group having 1 to 6 carbon atoms, and s representing an integer of 3 to 6.

The present invention also provides an organic electroluminescence device comprising a cathode, an anode and an organic thin film layer which is disposed between the cathode and the anode and comprises at least one layer comprising at least a light emitting layer, wherein at least one layer in the organic thin film layer comprises an aromatic amine derivative described above singly or as a component of a mixture.

THE EFFECT OF THE INVENTION

The EL device using the aromatic amine derivative of the present invention has a long life in combination with a sustained great efficiency of light emission.

THE MOST PREFERRED EMBODIMENT TO CARRY OUT THE INVENTION

The aromatic amine derivative of the present invention is represented by the following general formula (1):

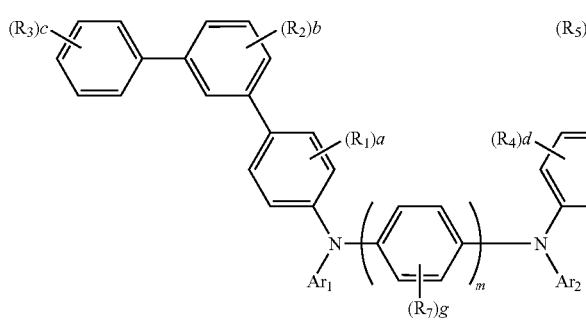

In general formula (1), $R_1$ to $R_6$ each independently represent a substituted or unsubstituted alkyl group having 1 to 10 carbon atoms, a substituted or unsubstituted alkoxyl group having 1 to 10 carbon atoms or a substituted or unsubstituted phenyl group, and $R_7$ represents a substituted or unsubstituted alkyl group having 1 to 10 carbon atoms or a substituted or unsubstituted alkoxyl group having 1 to 10 carbon atoms.

Examples of the alkyl group represented by $R_1$ to $R_7$ include methyl group, ethyl group, propyl group, isopropyl group, n-butyl group, s-butyl group, isobutyl group, t-butyl group, n-pentyl group, n-hexyl group, n-heptyl group, n-octyl group, hydroxymethyl group, 1-hydroxyethyl group, 2-hydroxyethyl group, 2-hydroxyisobutyl group, 1,2-dihydroxyethyl group, 1,3-dihydroxyisopropyl group, 2,3-dihydroxy-t-butyl group, 1,2,3-tri-hydroxypropyl group, chloromethyl group, 1-chloroethyl group, 2-chloroethyl group, 2-chloroisobutyl group, 1,2-dichloroethyl group, 1,3-dichloroisopropyl group, 2,3-dichloro-t-butyl group, 1,2,3-trichloropropyl group, bromomethyl group, 1-bromoethyl group, 2-bromoethyl group, 2-bromoisobutyl group, 1,2-dibromoethyl group, 1,3-dibromo-isopropyl group, 2,3-dibromo-t-butyl group, 1,2,3-tribromopropyl group, iodomethyl group, 1-iodoethyl group, 2-iodoethyl group, 2-iodoisobutyl group, 1,2-diiodoethyl group, 1,3-diiodoisopropyl group, 2,3-diiodo-t-butyl group, 1,2,3-triiodopropyl group, aminomethyl group, 1-aminoethyl group, 2-aminoethyl group, 2-aminoisobutyl group, 1,2-diaminoethyl group, 1,3-diaminoisopropyl group, 2,3-diamino-t-butyl group, 1,2,3-triamino-propyl group, cyanomethyl group, 1-cyanoethyl group, 2-cyanoethyl group, 2-cyanoisobutyl group, 1,2-dicyanoethyl group, 1,3-dicyanoisopropyl group, 2,3-dicyano-t-butyl group, 1,2,3-tricyanopropyl group, nitromethyl group, 1-nitroethyl group, 2-nitroethyl group, 2-nitroisobutyl group, 1,2-dinitroethyl group, 1,3-dinitroisopropyl group, 2,3-dinitro-t-butyl group and 1,2,3-trinitropropyl group.

The alkoxyl group represented by $R_1$ to $R_7$ is a group represented by —OY. Examples of the group represented by Y include the groups described above as the examples of the alkyl group.

In general formula, a, b, d, e and g each represent an integer of 0 to 4, c and f each represent an integer of 0 to 5, and m represents an integer of 1 to 3.

In general formula (1), it is preferable that b and e both represent 1, and $R_2$ and $R_5$ both represent phenyl group. It is more preferable that b and e both represent 1, and $R_2$ and $R_5$ both represent phenyl group having the bonding position at the m-position thereof.

In general formula (1), $Ar_1$ and $Ar_2$ each represent a group represented by following general formula (2), (3) or (4):

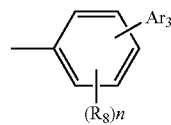

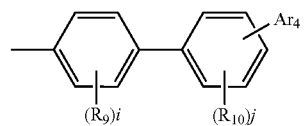

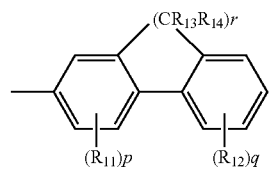

In general formula (2), $R_8$ represents a substituted or unsubstituted alkyl group having 1 to 10 carbon atoms, a substituted or unsubstituted alkoxyl group having 1 to 10 carbon atoms or a substituted or unsubstituted phenyl group. Examples of the alkyl group and the alkoxyl group include the groups described above as the examples of the alkyl group and the alkoxyl group, respectively, represented by $R_1$ to $R_7$.

In general formula (2), n represents an integer of 0 to 4.

In general formula (2), $Ar_3$ represents a substituted or unsubstituted phenyl group, a substituted or unsubstituted α-naphthyl group, a substituted or unsubstituted β-naphthyl group or an ortho-(o-), meta-(m-) or para-(p-)biphenyl group and preferably a substituted or unsubstituted α-naphthyl group or a substituted or unsubstituted β-naphthyl group. The bonding position of the group represented by $Ar_3$ at the benzene ring is the O-position or the m-position and preferably the m-position.

In general formula (2), it is preferable that $Ar_3$ represents a substituted or unsubstituted α-naphthyl group, and the bonding position thereof is the p-position. It is more preferable that the bonding position of the group represented by $Ar_3$ is the m-position, n represents 1, and $R_8$ represents phenyl group, the bonding position thereof being the m-position.

In general formula (3), $R_9$ and $R_{10}$ each independently represent a substituted or unsubstituted alkyl group having 1 to 10 carbon atoms, a substituted or unsubstituted alkoxyl group having 1 to 10 carbon atoms or a substituted or unsubstituted phenyl group. Examples of the alkyl group and the alkoxyl group include the groups described above as the examples of the alkyl group and the alkoxyl group, respectively, represented by $R_1$ to $R_7$.

In general formula (3), $Ar_4$ represents a substituted or unsubstituted phenyl group, and the bonding position is the o- or p-position and preferably the p-position. i and j each represent an integer of 0 to 4.

In general formula (4), $R_{11}$ and $R_{12}$ each independently represents a substituted or unsubstituted alkyl group having 1 to 10 carbon atoms, a substituted or unsubstituted alkoxyl group having 1 to 10 carbon atoms or a substituted or unsubstituted phenyl group. Examples of the alkyl group and the alkoxyl group include the groups described above as the examples of the alkyl group and the alkoxyl group, respectively, represented by $R_1$ to $R_7$. p represents an integer of 0 to 3, and q represents an integer of 0 to 4.

In general formula (4), $R_{13}$ and $R_{14}$ each independently represent the single bond, hydrogen atom, a substituted or unsubstituted alkyl group having 1 to 6 carbon atoms or a group represented by following general formula (5). Examples of the alkyl group include groups in which the number of carbon atoms is in the above range among the groups described above as the examples of the alkyl group represented by $R_1$ to $R_7$. r represents an integer of 1 or 2 and preferably 1.

—(CR$_{15}$R$_{16}$)$_s$—           (5)

In general formula (5), $R_{15}$ and $R_{16}$ each independently represent hydrogen atom or a substituted or unsubstituted alkyl group having 1 to 6 carbon atoms, and s representing an integer of 3 to 6. Examples of the alkyl group include groups in which the number of carbon atoms is in the above range among the groups described above as the examples of the alkyl group represented by $R_1$ to $R_7$.

In general formula (1), it is preferable that numbers of nuclear carbon atoms in the groups represented by $Ar_1$ and $Ar_2$ in general formula (1) are each independently 7 to 17 and more preferably 12 to 16. It is most preferable that $Ar_1$ and $Ar_2$ both represent p-biphenyl group.

Examples of the substituent to the groups represented by $R_1$ to $R_{16}$ and $Ar_1$ to $Ar_4$ in general formulae (1) to (5) include substituted and unsubstituted aryl groups having 5 to 50 nuclear carbon atoms, substituted and unsubstituted alkyl groups having 1 to 50 carbon atoms, substituted and unsubstituted alkoxyl groups having 1 to 50 carbon atoms, substituted and unsubstituted aralkyl groups having 6 to 50 nuclear carbon atoms, substituted and unsubstituted aryloxyl groups having 5 to 50 nuclear carbon atoms, substituted and unsubstituted arylthio groups having 5 to 50 nuclear carbon atoms, substituted and unsubstituted alkoxycarbonyl groups having 1 to 50 carbon atoms, amino groups, halogen atoms, cyano group, nitro group, hydroxyl group and carboxyl group.

Among these groups, alkyl groups having 1 to 10 carbon atoms, cycloalkyl groups having 5 to 7 carbon atoms and alkoxyl groups having 1 to 10 carbon atoms are preferable, alkyl groups having 1 to 6 carbon atoms and cycloalkyl groups having 5 to 7 carbon atoms are more preferable, and methyl group, ethyl group, n-propyl group, isopropyl group, n-butyl group, sec-butyl group, tert-butyl group, n-pentyl group, n-hexyl group, cyclopentyl group and cyclohexyl group are most preferable.

It is preferable that the aromatic amine derivative of the present invention is a material for organic electroluminescence devices and more preferably a hole transporting material for organic electroluminescence devices.

Examples of the aromatic amine derivative represented by general formula (1) of the present invention are shown in the following. However, the aromatic amine derivative is not limited to the compounds shown as the examples.

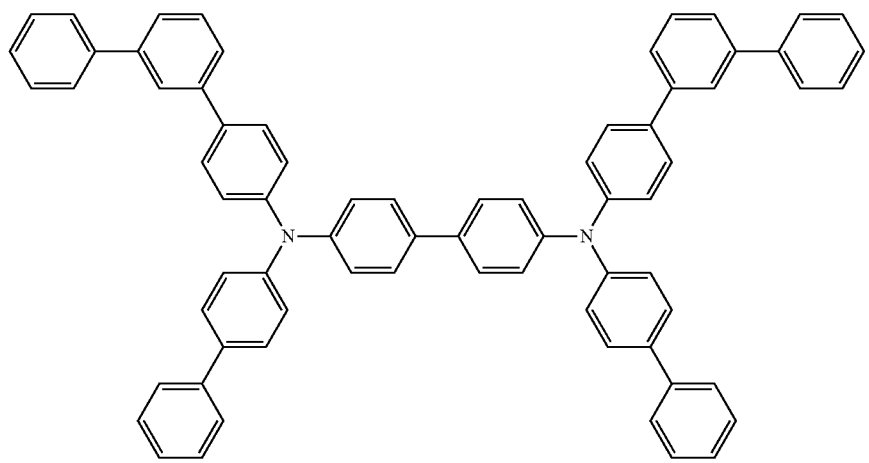

H1

-continued
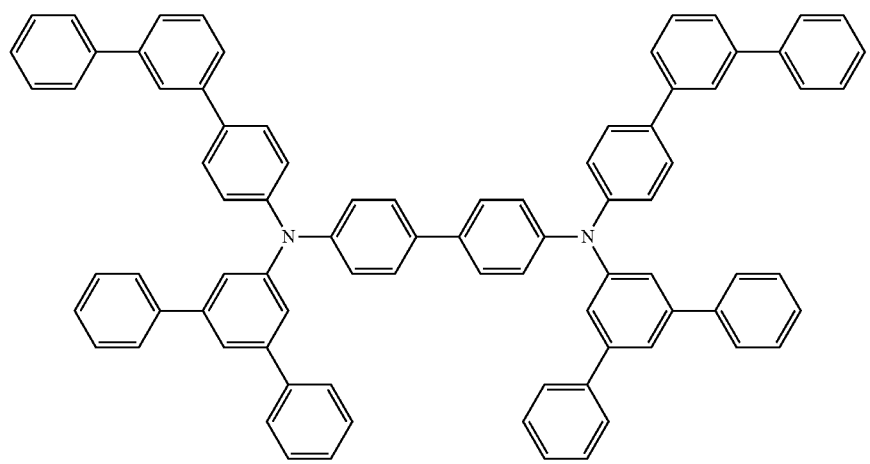
H2
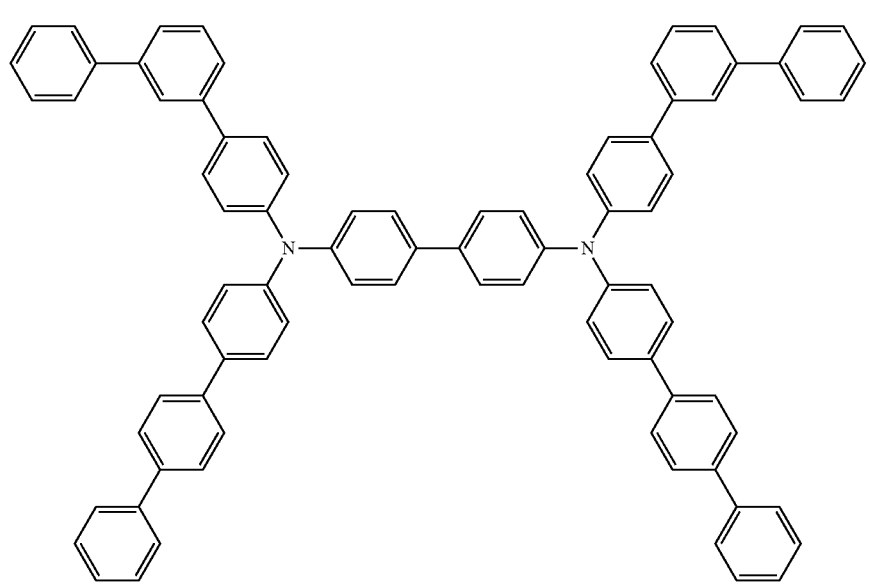
H3
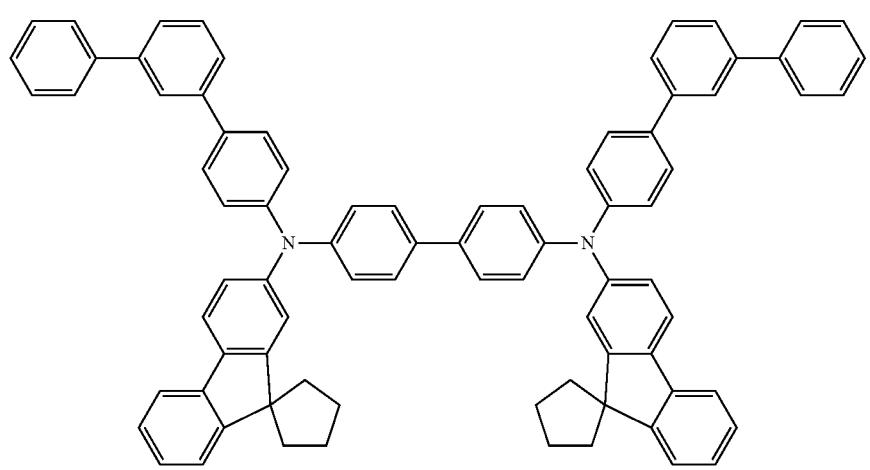
H4

-continued
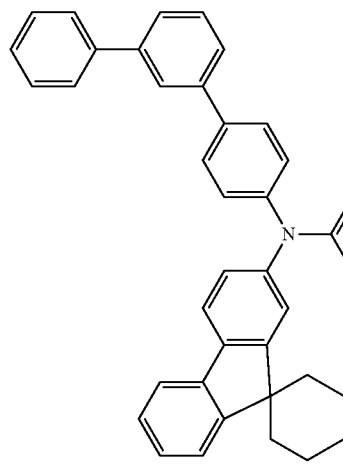
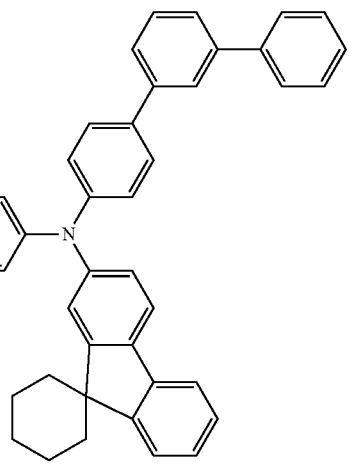
H5
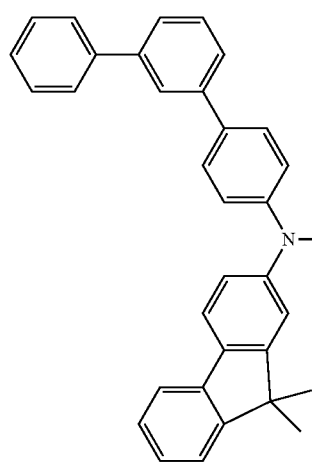
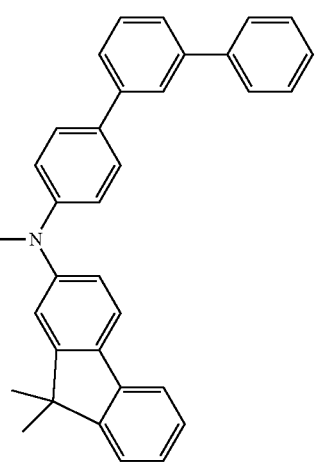
H6
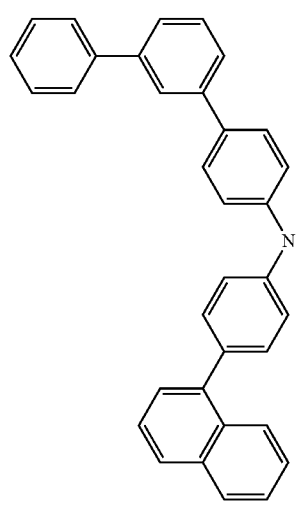
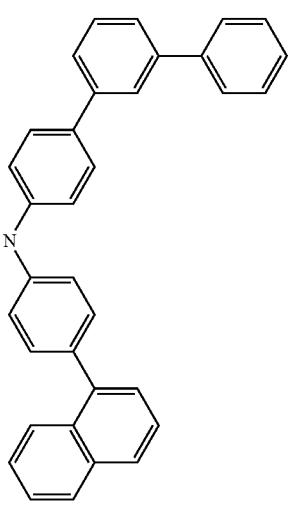
H7

-continued

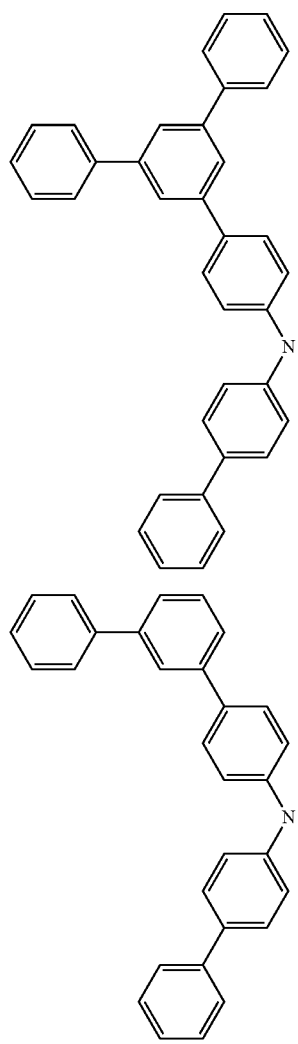

H8

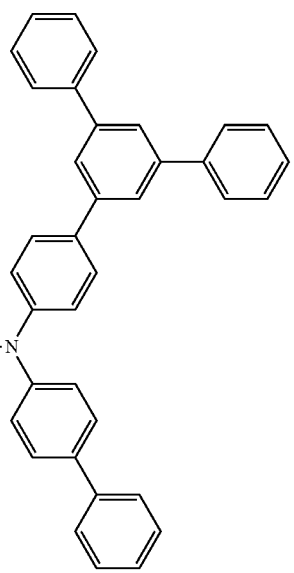

H9

The organic EL device of the present invention will be described in the following.

The organic electroluminescence device of the present invention comprises a cathode, an anode and an organic thin film layer which is disposed between the cathode and the anode and comprises at least one layer comprising at least the light emitting layer, wherein at least one layer in the organic thin film layer comprises the aromatic amine derivative described above singly or as a component of a mixture.

It is preferable that, in the organic EL device of the present invention, the organic thin film layer comprises a hole transporting layer, and the hole transporting layer comprises the aromatic amine derivative of the present invention singly or as a component of a mixture. It is more preferable that the hole transporting layer comprises the aromatic amine derivative of the present invention as the main component.

It is preferable that the aromatic amine derivative of the present invention is used for an organic EL device emitting bluish light.

It is preferable that, in the organic EL device of the present invention, the light emitting layer comprises an arylamine compound and/or a styrylamine compound.

Examples of the styrylamine compound include compounds represented by the following general formula (A):

(A)

In general formula (A), $Ar_8$ represents a group selected from phenyl group, biphenyl group, terphenyl group, stilbene group and distyrylaryl groups, $Ar_9$ and $Ar_{10}$ each represent hydrogen atom or an aromatic hydrocarbon group having 6 to 20 carbon atoms, the groups represented by $Ar_9$ and $Ar_{10}$ may be substituted, and p' represents an integer of 1 to 4. It is preferable that at least one of the groups represented by $Ar_9$ and/or $Ar_{10}$ is substituted with styryl group.

As the aromatic hydrocarbon group having 6 to 20 carbon atoms, phenyl group, naphthyl group, anthranyl group, phenanthryl group and terphenyl group are preferable.

Examples of the arylamine compound include compounds represented by the following general formula (B):

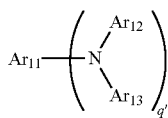
(B)

In general formula (B), $Ar_{1l}$ to $Ar_{13}$ each represent an aryl group having 5 to 40 nuclear carbon atoms which may be substituted, and q' represents an integer of 1 to 4.

As the aryl group having 5 to 40 nuclear carbon atoms, phenyl group, naphthyl group, anthranyl group, phenanthryl group, pyrenyl group, coronyl group, biphenyl group, terphenyl group, pyrrolyl group, furanyl group, thiophenyl group, benzothiophenyl group, oxadiazolyl group, diphenylanthranyl group, indolyl group, carbazolyl group, pyridyl group, benzoquinolyl group, fluoranthenyl group, acenaphtho-fluoranthenyl group and stilbene group are preferable. The aryl group having 5 to 40 nuclear carbon atoms may be substituted with substituents. Preferable examples of the substituent include alkyl groups having 1 to 6 carbon atoms such as ethyl group, methyl group, i-propyl group, n-propyl group, s-butyl group, t-butyl group, pentyl group, hexyl group, cyclopentyl group and cyclohexyl group; alkoxyl groups having 1 to 6 carbon atoms such as ethoxyl group, methoxyl group, i-propoxyl group, n-propoxyl group, s-butoxyl group, t-butoxyl group, pentoxyl group, hexyloxyl group, cyclopentoxyl group and cyclohexyloxyl group; aryl groups having 5 to 40 nuclear carbon atoms; amino groups substituted with an aryl group having 5 to 40 nuclear carbon atoms; ester groups having an aryl group having 5 to 40 nuclear carbon atoms; ester groups having an alkyl group having 1 to 6 carbon atoms; cyano group; nitro group; and halogen atoms such as chlorine atom, bromine atom and iodine atom.

The construction of the organic EL device of the present invention will be described in the following.

(1) Construction of the Organic EL Device

Typical examples of the construction of the organic EL device include:
(1) An anode/a light emitting layer/a cathode;
(2) An anode/a hole injecting layer/a light emitting layer/a cathode;
(3) An anode/a light emitting layer/an electron injecting layer/a cathode;
(4) An anode/a hole injecting layer/a light emitting layer/an electron injecting layer/a cathode;
(5) An anode/an organic semiconductor layer/a light emitting layer/a cathode;
(6) An anode/an organic semiconductor layer/an electron barrier layer/a light emitting layer/a cathode;
(7) An anode/an organic semiconductor layer/a light emitting layer/an adhesion improving layer/a cathode;
(8) An anode/a hole injecting layer/a hole transporting layer/a light emitting layer/an electron injecting layer/a cathode;
(9) An anode/an insulating layer/a light emitting layer/an insulating layer/a cathode;
(10) An anode/an inorganic semiconductor layer/an insulating layer/a light emitting layer/an insulating layer/a cathode;
(11) An anode/an organic semiconductor layer/an insulating layer/a light emitting layer/an insulating layer/a cathode;
(12) An anode/an insulating layer/a hole injecting layer/a hole transporting layer/a light emitting layer/an insulating layer/a cathode; and
(13) An anode/an insulating layer/a hole injecting layer/a hole transporting layer/a light emitting layer/an electron injecting layer/a cathode.

In general, construction (8) is preferable among the above constructions. However, the construction is not limited to those described as the examples.

The aromatic amine derivative of the present invention may be used in any layer in the organic thin film layer of the organic EL device. The aromatic amine derivative can be used in the light emitting zone or the hole transporting zone. It is preferable that the aromatic amine derivative is used in the hole transporting zone and, more preferably, in the hole transporting layer since crystallization of the molecules can be suppressed, and the yield in the production of the organic EL device can be increased.

It is preferable that the organic thin film layer comprises 30 to 100% by mole of the aromatic amine derivative of the present invention.

(2) Substrate which Transmits Light

The organic EL device of the present invention is prepared on a substrate which transmits light. The substrate which transmits light is the substrate which supports the organic EL device. It is preferable that the substrate which transmits light has a transmittance of light of 50% or greater in the visible region of 400 to 700 nm and is flat and smooth.

Examples of the substrate which transmits light include glass plates and polymer plates. Specific examples of the glass plate include plates made of soda ash glass, glass containing barium and strontium, lead glass, aluminosilicate glass, borosilicate glass, barium borosilicate glass and quartz. Specific examples of the polymer plate include plates made of polycarbonate resins, acrylic resins, polyethylene terephthalate resins, polyether sulfide resins and polysulfone resins.

(3) Anode

The anode in the organic EL device of the present invention has the function of injecting holes into the hole transporting layer or the light emitting layer. It is effective that the anode has a work function of 4.5 eV or greater. Examples of the material for the anode include indium tin oxide alloys (ITO), tin oxide (NESA), indium-zinc oxides (IZO), gold, silver, platinum and copper.

The anode can be prepared by forming a thin film of the electrode material described above in accordance with a process such as the vapor deposition process and the sputtering process.

When the light emitted from the light emitting layer is obtained through the anode, it is preferable that the anode has a transmittance of the emitted light greater than 10%. It is also preferable that the sheet resistivity of the anode is several hundred $\Omega/\square$ or smaller. The thickness of the anode is, in general, selected in the range of 10 nm to 1 μm and preferably in the range of 10 to 200 nm although the preferable range may be different depending on the used material.

(4) Light Emitting Layer

The light emitting layer in the organic EL device has a combination of the following functions:
(1) The injecting function: the function of injecting holes from the anode or the hole injecting layer and injecting electrons from the cathode or the electron injecting layer when an electric field is applied;
(2) The transporting function: the function of transporting injected charges (electrons and holes) by the force of the electric field; and
(3) The light emitting function: the function of providing the field for recombination of electrons and holes and leading the recombination to the emission of light.

The easiness of injection may be different between holes and electrons. The ability of transportation expressed by the mobility may be different between holes and electrons. It is preferable that either one of the charges is transferred.

As the process for forming the light emitting layer, a conventional process such as the vapor deposition process, the spin coating process and the LB process can be used. It is particularly preferable that the light emitting layer is a molecular deposit film. The molecular deposit film is a thin film formed by deposition of a material compound in the gas phase or a thin film formed by solidification of a material compound in a solution or in the liquid phase. In general, the molecular deposit film can be distinguished from the thin film formed in accordance with the LB process (the molecular accumulation film) based on the differences in the aggregation structure and higher order structures and functional differences caused by these structural differences.

As disclosed in Japanese Patent Application Laid-Open No. Showa 57(1982)-51781, the light emitting layer can also be formed by dissolving a binder such as a resin and the material compounds into a solvent to prepare a solution, followed by forming a thin film from the prepared solution in accordance with the spin coating process or the like.

When the aromatic amine derivative of the present invention is used as the light emitting material of the light emitting layer, the light emitting layer may further comprise other conventional light emitting materials, or a light emitting layer comprising other conventional light emitting materials may be laminated to the light emitting layer comprising the light emitting material comprising the aromatic amine derivative of the present invention.

Examples of the host material and the doping material which can be used for the light emitting layer in combination with the aromatic amine derivative of the present invention include anthracene, naphthalene, phenanthrene, pyrene, tetracene, coronene, chrysene, fluorescein, perylene, phthaloperylene, naphthaloperylene, perynone, phthaloperynone, naphthaloperynone, diphenylbutadiene, tetraphenyl-butadiene, coumarine, oxadiazole, aldazine, bisbenzoxazoline, bis-styryl, pyrazine, cyclopentadiene, metal complex compounds of quinoline, metal complex compounds of aminoquinoline, metal complex compounds of benzoquinoline, imine, diphenylethylene, vinylanthracene, diamino-carbazole, pyran, thiopyran, polymethine, melocyanine, oxinoid compounds chelated with imidazole, quinacridone, rubrene and fluorescent coloring agents. However, the light emitting material and the doping material are not limited to the compounds described above.

As the host material which can be used in the light emitting layer in combination with the aromatic amine derivative of the present invention, compounds represented by the following general formulae (i) to (ix) are preferable.

Asymmetric anthracenes represented by the following general formula (i):

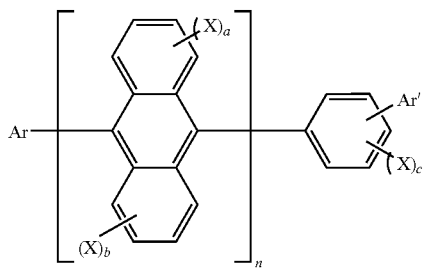

(i)

In the above general formula, Ar represents a substituted or unsubstituted condensed aromatic group having 10 to 50 nuclear carbon atoms.

Ar' represents a substituted or unsubstituted aromatic group having 6 to 50 nuclear carbon atoms.

X represents a substituted or unsubstituted aromatic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, carboxyl group, a halogen atom, cyano group, nitro group or hydroxy group.

a, b and c each represent an integer of 0 to 4.

n represents an integer of 1 to 3. When n represents a number of 2 or greater, a plurality of groups shown in [ ] may be the same with or different from each other.

Asymmetric monoanthracene derivatives represented by the following general formula (ii):

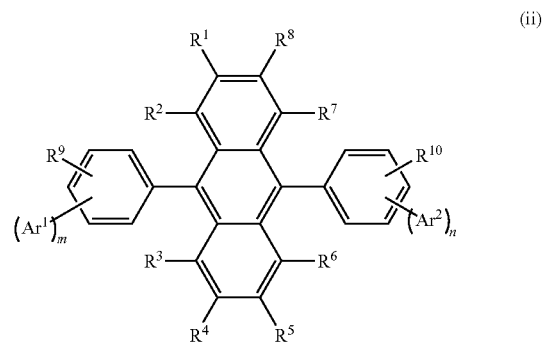

(ii)

In the above general formula, $Ar^1$ and $Ar^2$ each independently represent a substituted or unsubstituted aromatic cyclic group having 6 to 50 nuclear carbon atoms, and m and n each represents an integer of 1 to 4. When m=n=1 and the positions of bonding of the groups represented by $Ar^1$ and $Ar^2$ to the benzene rings at the left side and at the right side, respectively, are symmetric, $Ar^1$ and $Ar^2$ do not represent the same group. When m or n represents an integer of 2 to 4, m and n represent integers different from each other.

$R^1$ to $R^{10}$ each independently represent hydrogen atom, a substituted or unsubstituted aromatic cyclic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, a substituted or unsubstituted silyl group, carboxyl group, a halogen atom, cyano group, nitro group or hydroxyl group.

Asymmetric pyrene derivatives represented by the following general formula (iii):

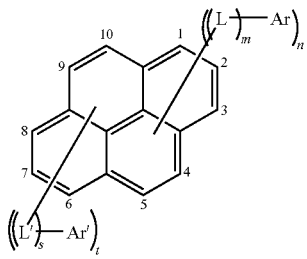

(iii)

In the above general formula, Ar and Ar' each represent a substituted or unsubstituted aromatic group having 6 to 50 nuclear carbon atoms.

L and L' each represent a substituted or unsubstituted phenylene group, a substituted or unsubstituted naphthalenylene group, a substituted or unsubstituted fluorenylene group or a substituted or unsubstituted dibenzosilolylene group.

m represents an integer of 0 to 2, n represents an integer of 1 to 4, s represents an integer of 0 to 2, and t represents an integer of 0 to 4.

The group represented by L or Ar is bonded at one of 1 to 5 positions of pyrene, and the group represented by L' or Ar' is bonded at one of 6 to 10 positions of pyrene When n+t is an even number, the groups represented by Ar, Ar', L and L' satisfy the following condition (1) or (2):

(1) Ar≠Ar' and/or L≠L' (≠ means the groups have structures different from each other)

(2) When Ar=Ar' and L=L', (2-1) m≠s and/or n≠t, or (2-2) When m=s and n=t, the case where the positions of substitution of L and L' or Ar and Ar' on pyrene are the 1-position and the 6-position, respectively, or the 2-position and the 7-position, respectively, is excluded when (2-2-1) L and L' or two positions on pyrene are bonded at different bonding positions on Ar and Ar', respectively, or (2-2-2) L and L' or two positions on pyrene are bonded at the same bonding position on Ar and Ar', respectively.

Asymmetric anthracene derivatives represented by the following general formula (Iv):

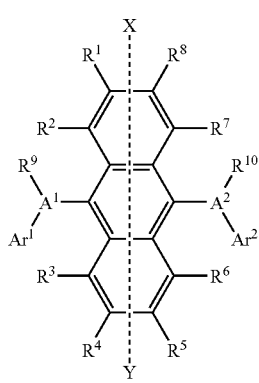

(iv)

In the above general formula, $A^1$ and $A^2$ each independently represent a substituted or unsubstituted condensed aromatic cyclic group having 10 to 20 nuclear carbon atoms.

$Ar^1$ and $Ar^2$ each independently represent hydrogen atom or a substituted or unsubstituted aromatic cyclic group having 6 to 50 nuclear carbon atoms.

$R^1$ to $R^{10}$ each independently represent hydrogen atom, a substituted or unsubstituted aromatic cyclic group having 6 to 50 nuclear carbon atoms, a substituted or unsubstituted aromatic heterocyclic group having 5 to 50 nuclear atoms, a substituted or unsubstituted alkyl group having 1 to 50 carbon atoms, a substituted or unsubstituted cycloalkyl group, a substituted or unsubstituted alkoxyl group having 1 to 50 carbon atoms, a substituted or unsubstituted aralkyl group having 6 to 50 carbon atoms, a substituted or unsubstituted aryloxyl group having 5 to 50 nuclear atoms, a substituted or unsubstituted arylthio group having 5 to 50 nuclear atoms, a substituted or unsubstituted alkoxycarbonyl group having 1 to 50 carbon atoms, a substituted or unsubstituted silyl group, carboxyl group, a halogen atom, cyano group, nitro group or hydroxyl group.

$Ar^1$, $Ar^2$, $R^9$ and $R^{10}$ may each be present in a plurality of numbers. Adjacent atoms and groups among the atoms and the groups represented by $Ar^1$, $Ar^2$, $R^9$ and $R^{10}$ may be bonded to each other to form a saturated or unsaturated cyclic structure.

The case where the groups are bonded to the 9- and 10-positions of anthracene in general formula (1) to form a symmetric structure with respect to line X-Y is excluded.

Anthracene derivatives represented by the following general formula (v):

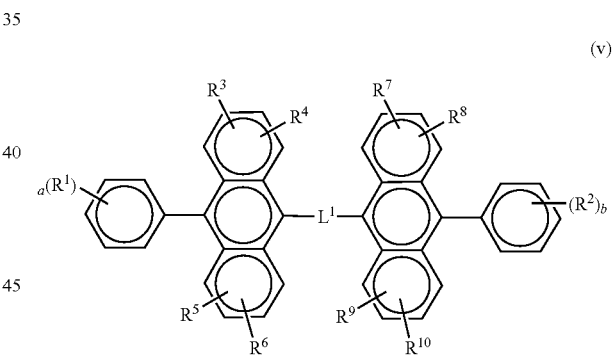

(v)

In the above general formula, $R^1$ to $R^{10}$ each independently represent hydrogen atom, an alkyl group, a cycloalkyl group, an aryl group which may be substituted, an alkoxyl group, an aryloxyl group, an alkylamino group, an alkenyl group, an arylamino group or a heterocyclic group which may be substituted. a and b each represent an integer of 1 to 5. When a or b represents an integer of 2 or greater, the atoms and the groups represented by a plurality of $R^1$ or by a plurality of $R^2$, respectively, may be the same with or different from each other or may be bonded to each other to form a ring. The atoms and the groups represented by the pair of $R^3$ and $R^4$, $R^5$ and $R^6$, $R^7$ and $R^8$ or $R^9$ and $R^{10}$ may be bonded to each other to form a ring. $L^1$ represents the single bond, —O—, —S—. —N(R)— (R representing an alkyl group or an aryl group which may be substituted), an alkylene group or an arylene group.

Anthracene derivatives represented by the following general formula (vi):

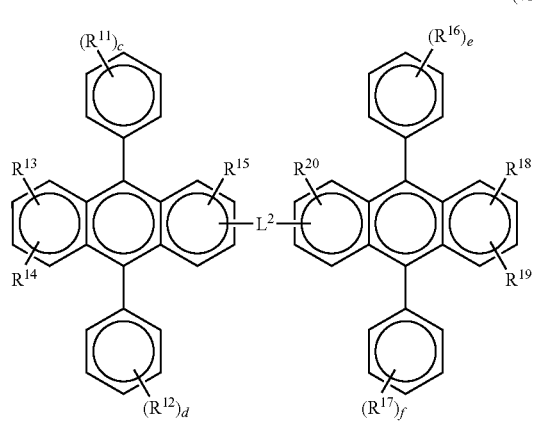

(vi)

In the above general formula, $R^{11}$ to $R^{20}$ each independently represent hydrogen atom, an alkyl group, a cycloalkyl group, an aryl group, an alkoxyl group, an aryloxyl group, an alkylamino group, an arylamino group or a heterocyclic group which may be substituted. c, d, e and f each represent an integer of 1 to 5. When c, d, e or f represents an integer of 2 or greater, the atoms and the groups represented by the plurality of $R^{11}$, by the plurality of $R^{12}$, by the plurality of $R^{16}$ or by the plurality of $R^{17}$, respectively, may be the same with or different from each other or may be bonded to each other to form a ring. The atoms and the groups represented by the pair of $R^{13}$ and $R^{14}$ or the pair of $R^{18}$ and $R^{19}$ may be bonded to each other to form a ring. $L^2$ represents the single bond, —O—, —S—, —N(R)— (R representing an alkyl group or an aryl group which may be substituted), an alkylene group or an arylene group.

Spirofluorene derivatives represented by the following general formula (vii):

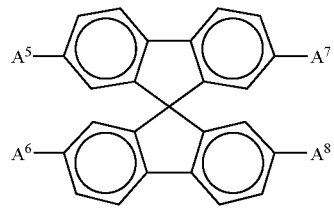

(vii)

In the above general formula, $A^5$ to $A^8$ each independently represent a substituted or unsubstituted biphenyl group or a substituted or unsubstituted naphthyl group.

Compounds having a condensed ring represented by the following general formula (viii):

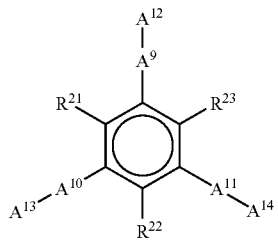

(viii)

In the above general formula, $A^9$ to $A^{14}$ are as defined above. $R^{21}$ to $R^{23}$ each independently represent hydrogen atom, an alkyl group having 1 to 6 carbon atoms, a cycloalkyl group having 3 to 6 carbon atoms, an alkoxyl group having 1 to 6 carbon atoms, an aryloxyl group having 5 to 18 carbon atoms, an aralkyloxyl group having 7 to 18 carbon atoms, an arylamino group having 5 to 16 carbon atoms, nitro group, cyano group, an ester group having 1 to 6 carbon atoms or a halogen atom. At least one of $A^9$ to $A^{14}$ represent a group having condensed aromatic rings having 3 or more rings.

Fluorene compounds represented by the following general formula (ix):

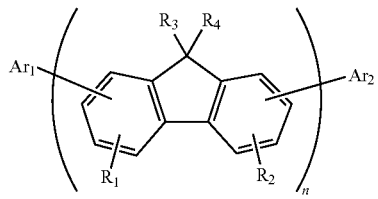

(ix)

In the above general formula, $R_1$ and $R_2$ each represent hydrogen atom, a substituted or unsubstituted alkyl group, a substituted or unsubstituted aralkyl group, a substituted or unsubstituted aryl group, a substituted or unsubstituted heterocyclic group, a substituted amino group, cyano group or a halogen atom. The atoms and the groups represented by a plurality of $R_1$ or by a plurality of $R_2$ each bonded to different fluorene groups may be the same with or different from each other. The atoms and the groups represented by $R_1$ and $R_2$ each bonded to the same fluorene group may be the same with or different from each other. $R_3$ and $R_4$ each represent hydrogen atom, a substituted or unsubstituted alkyl group, a substituted or unsubstituted aralkyl group, a substituted or unsubstituted aryl group or a substituted or unsubstituted heterocyclic group. The atoms and the groups represented by a plurality of $R_3$ or by a plurality of $R_4$ each bonded to different fluorene groups may be the same with or different from each other. The atoms and the groups represented by $R_3$ and $R_4$ each bonded to the same fluorene group may be the same with or different from each other. $Ar_1$ and $Ar_2$ each represent a substituted or unsubstituted condensed polycyclic aromatic group having 3 or more benzene rings in the entire molecule or a substituted or unsubstituted polycyclic heterocyclic group having 3 or more rings in the entire molecule as the total of the benzene ring and heterocyclic rings which is bonded to fluorene group via carbon atom. The groups represented by $Ar^1$ and $Ar^2$ may be the same with or different from each other. n represents an integer of 1 to 10.

Among the above host materials, the anthracene derivatives are preferable, monoanthracene derivatives are more preferable, and asymmetric anthracene derivatives are most preferable.

As the light emitting material of the dopant, a compound emitting phosphorescent light may be used. As for the compound emitting phosphorescent light, it is preferable that a compound having carbazole ring is used as the host compound. A compound which can emit light from the triplet excimer is used as the dopant. The dopant is not particularly limited as long as light is emitted from the triplet excimer. Metal complexes having at least one metal selected from Ir, Ru, Pd, Pt, Os and Re are preferable, and porphyrin metal complexes and complexes formed into ortho metals are more preferable.

The host compound preferably used for emitting phosphorescent light from a compound having carbazole ring is a compound exhibiting the function of emitting light from a phosphorescent light emitting compound as the result of energy transfer from the excited state to the phosphorescent light emitting compound. The host compound is not particularly limited as long as the energy of the excimer can be transferred to the phosphorescent light emitting compound and can be suitably selected in accordance with the object. The host compound may have a desired hetero ring other than carbazole ring.

Examples of the host compound include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, chalcone derivatives substituted with an amine, styrylanthracene derivatives, fluorenone derivatives, hydrazone derivatives, stilbene derivatives, silazane derivatives, aromatic tertiary amine compounds, styrylamine compounds, aromatic dimethylidine-based compounds, porphyrin-based compounds, anthraquinodimethane derivatives, anthrone derivatives, diphenylquinone derivatives, thiopyrane dioxide derivatives, carbodiimide derivatives, fluorenylidenemethane derivatives, distyryl-pyrazine derivatives, anhydrides of heterocyclic tetracarboxylic acids derived from naphthalene, perylene and the like, phthalocyanine derivatives, metal complexes such as metal complexes of 8-quinolinol derivatives, metal phthalocyanines and metal complexes using benzoxazole and benzothiazole as the ligand, polysilane-based compounds, electrically conductive macromolecular oligomers such as poly (N-vinylcarbazole) derivatives, aniline-based copolymer, thiophene oligomers and polythiophene and macromolecular compounds such as polythiophene derivatives, polyphenylene derivatives, polyphenylene vinylene derivatives and polyfluorene derivatives. The host compound may be used singly or in combination of two or more.

Examples of the host compound include the compounds shown in the following:

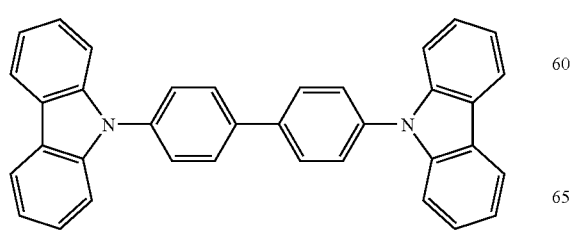

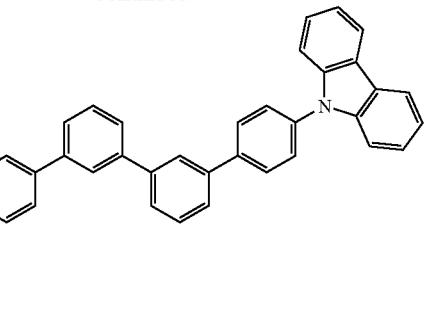

-continued

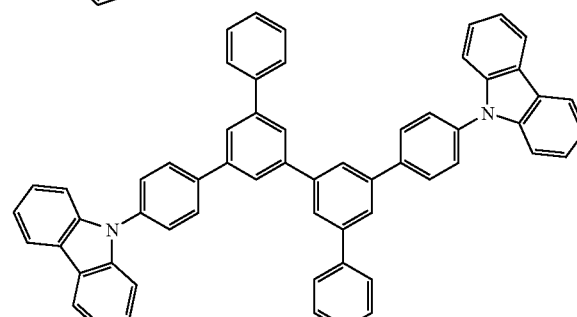

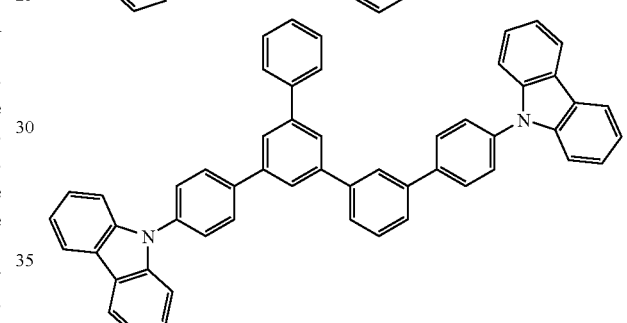

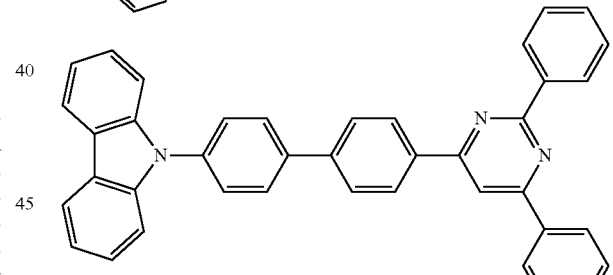

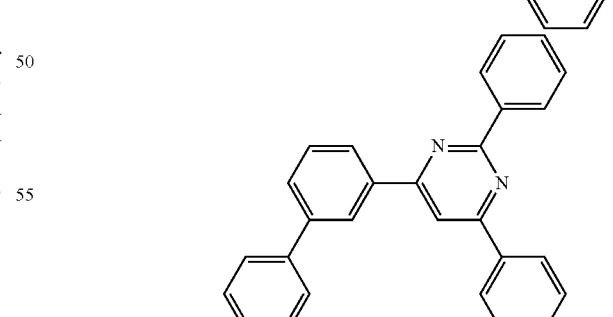

The dopant emitting phosphorescent light is a compound which can emit light from the triplet excimer. The dopant is not limited as long as light is emitted from the triplet excimer. Metal complexes having at least one metal selected from Ir, Ru, Pd, Pt, Os and Re are preferable, and porphyrin metal complexes and complexes formed into ortho metals are more preferable. As the porphyrin metal complex, porphyrin platinum complexes are preferable. The compound emitting phosphorescent light may be used singly or in combination of two or more.

As the ligand forming the complexes formed into ortho metals, various ligands can be used. Examples of the preferable ligand include 2-phenylpyridine derivatives, 7,8-benzoquinoline derivatives, 2-(2-thienyl)pyridine derivatives, 2-(1-naphthyl)pyridine derivatives and 2-phenylquinoline derivatives. These derivatives may have substituents, where necessary. In particular, fluorides and ligands having trifluoro-methyl group are preferable for the dopant emitting bluish light. Ligands other than those described above such as acetyl acetonates and picric acid may be present as the auxiliary ligand.

The content of the dopant emitting phosphorescent light in the light emitting layer is not particularly limited and can be suitably selected in accordance with the object. The content is, for example, 0.1 to 70% by mass and preferably 1 to 30% by mass. When the content is smaller than 0.1% by mass, the light emission is weak, and the effect of using the dopant is not exhibited. When the content exceeds 70% by mass, the phenomenon called concentration quenching arises markedly, and the property of the device deteriorates.

The light emitting layer may further comprise a hole transporting material, electron transporting material and a polymer binder, where necessary.

The thickness of the light emitting layer is preferably 5 to 50 nm, more preferably 7 to 50 nm and most preferably 10 to 50 nm. When the thickness is smaller than 5 nm, the formation of the light emitting layer becomes difficult, and there is the possibility that the adjustment of the chromaticity becomes difficult. When the thickness exceeds 50 nm, there is the possibility that the driving voltage increases.

(5) Hole Injecting and Transporting Layer (Hole Transporting Zone)

The hole injecting and transporting layer is a layer which helps injection of holes into the light emitting layer and transports the holes to the light emitting region. The layer exhibits a great mobility of holes and, in general, has an ionization energy as small as 5.5 eV or smaller. For the hole injecting and transporting layer, a material which transports holes to the light emitting layer under an electric field of a smaller strength is preferable. A material which exhibits, for example, a mobility of holes of at least $10^{-4}$ $cm^2/V \cdot second$ under application of an electric field of $10^4$ to $10^6$ V/cm is preferable.

When the aromatic amine derivative of the present invention is used for the hole transporting zone, the hole injecting and transporting layer may be formed with the aromatic amine derivative of the present invention alone or with a mixture comprising the aromatic amine derivative of the present invention.

The material used in combination with the aromatic amine derivative of the present invention for forming the hole injecting and transporting layer is not particularly limited as long as the material has the above preferable properties. A material can be selected as desired from materials which are conventionally used as the charge transporting material of holes in photoconductive materials and conventional materials which are used for the hole injecting layer in organic EL devices.

Examples include triazole derivatives (U.S. Pat. No. 3,112,197), oxadiazole derivatives (U.S. Pat. No. 3,189,447), imidazole derivatives (Japanese Patent Application Publication No. Showa 37(1962)-16096), polyarylalkane derivatives (U.S. Pat. Nos. 3,615,402, 3,820,989 and 3,542,544; Japanese Patent Application Publication Nos. Showa 45(1970)-555 and Showa 51(1976)-10983; and Japanese Patent Application Laid-Open Nos. Showa 51(1976)-93224, Showa 55(1980)-17105, Showa 56(1981)-4148, Showa 55(1980)-108667, Showa 55(1980)-156953 and Showa 56(1981)-36656); pyrazoline derivatives and pyrazolone derivatives (U.S. Pat. Nos. 3,180,729 and 4,278,746; and Japanese Patent Application Laid-Open Nos. Showa 55(1980)-88064, Showa 55(1980)-88065, Showa 49(1974)-105537, Showa 55(1980)-51086, Showa 56(1981)-80051, Showa 56(1981)-88141, Showa 57(1982)-45545, Showa 54(1979)-112637 and Showa 55(1980)-74546); phenylenediamine derivatives (U.S. Pat. No. 3,615,404; Japanese Patent Application Publication Nos. Showa 51(1976)-10105, Showa 46(1971)-3712 and Showa 47(1972)-25336; and Japanese Patent Application Laid-Open Nos. Showa 54(1979)-53435, Showa 54(1979)-110536 and Showa 54(1979)-119925); arylamine derivatives (U.S. Pat. Nos. 3,567,450, 3,180,703, 3,240,597, 3,658,520, 4,232,103, 4,175,961 and 4,012,376; Japanese Patent Application Publication Nos. Showa 49(1974)-35702 and Showa 39(1964)-27577; Japanese Patent Application Laid-Open Nos. Showa 55(1980)-144250, Showa 56(1981)-119132 and Showa 56(1981)-22437; and West German Patent No. 1,110,518); chalcone derivatives substituted with amino group (U.S. Pat. No. 3,526,501); oxazole derivatives (U.S. Pat. No. 3,257,203); styrylanthracene derivatives (Japanese Patent Application Laid-Open Nos. Showa 56(1981)-46234); fluorenone derivatives (Japanese Patent Application Laid-Open Nos. Showa 54(1979)-110837); hydrazone derivatives (U.S. Pat. No. 3,717,462; and Japanese Patent Application Laid-Open Nos. Showa 54(1979)-59143, Showa 55(1980)-52063, Showa 55(1980)-52064, Showa 55(1980)-46760, Showa 55(1980)-85495, Showa 57(1982)-11350, Showa 57(1982)-148749 and Heisei 2(1990)-311591); stilbene derivatives (Japanese Patent Application Laid-Open Nos. Showa 61(1986)-210363, Showa 61(1986)-228451, Showa 61(1986)-14642, Showa 61(1986)-72255, Showa 62(1987)-47646, Showa 62(1987)-36674, Showa 62(1987)-10652, Showa 62(1987)-30255, Showa 60(1985)-93455, Showa 60(1985)-94462, Showa 60(1985)-174749 and Showa 60(1985)-175052); silazane derivatives (U.S. Pat. No. 4,950,950); polysilane-based compounds (Japanese Patent Application Laid-Open No. Heisei 2(1990)-204996); aniline-based copolymers (Japanese Patent Application Laid-Open No. Heisei 2(1990)-282263); and electrically conductive macromolecular oligomers (in particular, thiophene oligomers) disclosed in Japanese Patent Application Laid-Open No. Heisei 1(1989)-211399.

Besides the above materials which can be used as the material for the hole injecting layer, porphyrin compounds (compounds disclosed in Japanese Patent Application Laid-Open No. Showa 63(1988)-295695); and aromatic tertiary amine compounds and styrylamine compounds (U.S. Pat. No. 4,127,412 and Japanese Patent Application Laid-Open Nos. Showa 53(1978)-27033, Showa 54(1979)-58445, Showa 54(1979)-149634, Showa 54(1979)-64299, Showa 55(1980)-79450. Showa 55(1980)-144250, Showa 56(1981)-119132, Showa 61(1986)-295558, Showa 61(1986)-98353 and Showa 63(1988)-295695) are preferable, and the aromatic tertiary amines are more preferable.

Further examples include compounds having two condensed aromatic rings in the molecule which are described in the U.S. Pat. No. 5,061,569 such as 4,4'-bis(N-(1-naphthyl)-N-phenylamino)-biphenyl (referred to as NPD, hereinafter) and a compound in which three triphenylamine units are bonded together in a star-burst shape, which is described in Japanese Patent Application Laid-Open No. Heisei 4 (1992)-308688, such as 4,4',4''-tris(N-(3-methylphenyl)-N-phenylamino)-triphenylamine (referred to as MTDATA, hereinafter).

Besides the aromatic dimethylidine-based compounds shown above as the examples of the material for the light emitting layer, inorganic compounds such as Si of the p-type and SiC of the p-type can also be used as the material for the hole injecting and transporting layer.

The hole injecting and transporting layer can be formed by preparing a thin film of the aromatic amine derivative of the present invention in accordance with a conventional process such as the vacuum vapor deposition process, the spin coating process, the casting process and the LB process. The thickness of the hole injecting and transporting layer is not particularly limited. In general, the thickness is 5 nm to 5 μm. The hole injecting and transporting layer may be constituted with a single layer comprising one or more types of the materials described above or may be a laminate of the hole injecting and transporting layer described above and a hole injecting and transporting layer comprising different compounds from that used for the above hole injecting and transporting layer as long as the hole injecting and transporting zone comprises the aromatic amine derivative of the present invention.

An organic semiconductor layer may be disposed as a layer helping injection of holes or electrons into the light emitting layer. As the organic semiconductor layer, a layer having a conductivity of $10^{-10}$ S/cm or greater is preferable. As the material for the organic semiconductor layer, oligomers containing thiophene can be used, and conductive oligomers such as oligomers containing thiophene, oligomers containing allylamine disclosed in Japanese Patent Application Laid-Open No. Heisei 8 (1996)-193191 and conductive dendrimers such as dendrimers containing allylamine, can also be used.

(6) Electron Injecting and Transporting Layer

The electron injecting and transporting layer is a layer which helps injection of electrons into the light emitting layer and transportation of the electrons to the light emitting region and exhibits a great mobility of electrons. The adhesion improving layer is an electron injecting layer comprising a material exhibiting improved adhesion with the cathode.

It is known that, in an organic EL device, emitted light is reflected at an electrode (the cathode in the present case), and the light emitted and obtained directly from the anode and the light obtained after reflection at the electrode interfere with each other. The thickness of the electron transporting layer is suitably selected in the range of several nm to several μm so that the interference is effectively utilized. When the thickness is great, it is preferable that the mobility of electrons is at least $10^{-5}$ cm$^2$/Vs or greater under the application of an electric field of $10^4$ to $10^6$ V/cm so that the increase in the voltage is prevented.

As the material used for the electron injecting layer, metal complexes of 8-hydroxyquinoline and derivatives thereof and oxadiazole derivatives are preferable. Examples of 8-hydroxyquinoline and the derivative thereof include metal chelated oxinoid compounds including chelate compounds of oxines (in general, 8-quinolinol or 8-hydroxy-quinoline). For example, tris(8-quinolinol)aluminum can be used as the electron injecting material.

Examples of the oxadiazole derivative include electron transfer compounds represented by the following general formulae:

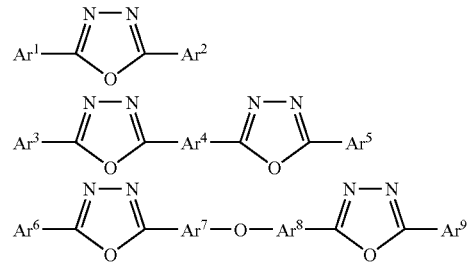

In the above formulae, $Ar^1$, $Ar^2$, $Ar^3$, $Ar^5$, $Ar^6$ and $Ar^9$ each represent a substituted or unsubstituted aryl group and may represent the same group or different groups. $Ar^4$, $Ar^7$ and $Ar^8$ each represent a substituted or unsubstituted arylene group and may represent the same group or different groups.

Examples of the aryl group include phenyl group, biphenyl group, anthranyl group, perylenyl group and pyrenyl group. Examples of the arylene group include phenylene group, naphthylene group, biphenylene group, anthranylene group, perylenylene group and pyrenylene group. Examples of the substituent include alkyl groups having 1 to 10 carbon atoms, alkoxyl groups having 1 to 10 carbon atoms and cyano group. As the electron transfer compound, compounds which can form thin films are preferable.

Specific examples of the electron transfer compound include the following compounds:

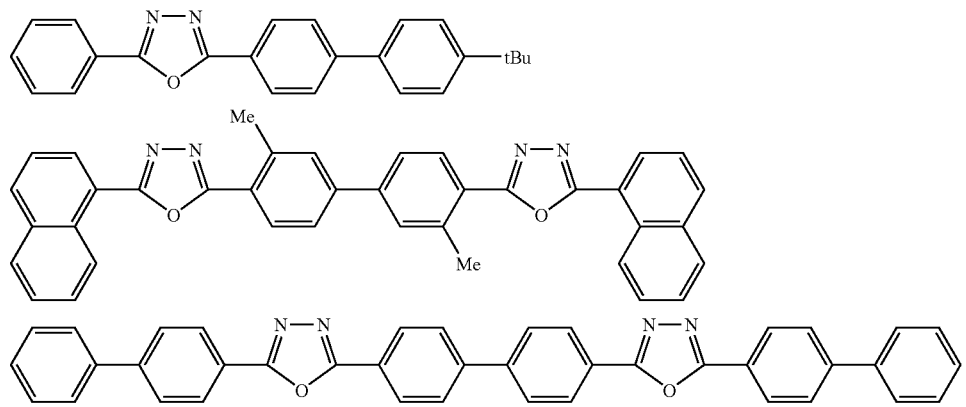

-continued

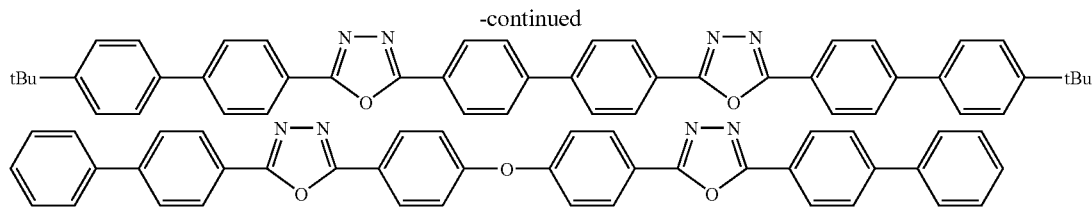

As the material which can be used for the electron injecting layer and the electron transporting layer, compounds represented by the following general formulae (A) to (F) can be used.

Heterocyclic derivatives having nitrogen atom represented by any one of general formulae (A) and (B):

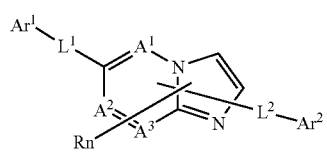

(A)

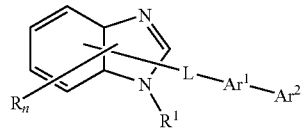

(B)

In general formulae (A) and (B), $A^1$ to $A^3$ each independently represent nitrogen atom or carbon atom.

$Ar^1$ represents a substituted or unsubstituted aryl group having 6 to 60 nuclear carbon atoms or a substituted or unsubstituted heteroaryl group having 3 to 60 nuclear carbon atoms; $Ar^2$ represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms, a substituted or unsubstituted alkoxyl group having 1 to 20 carbon atoms or a divalent group derived from any of the above groups; and either one of $Ar^1$ and $Ar^2$ represents a substituted or unsubstituted condensed cyclic group having 10 to 60 nuclear carbon atoms or a substituted or unsubstituted monohetero condensed cyclic group having 3 to 60 nuclear carbon atoms.

$L^1$, $L^2$ and L each independently represent the single bond, a substituted or unsubstituted arylene group having 6 to 60 nuclear carbon atoms, a substituted or unsubstituted heteroarylene group having 3 to 60 nuclear carbon atoms or a substituted or unsubstituted fluorenylene group.

R represents hydrogen atom, a substituted or unsubstituted aryl group having 6 to 60 nuclear carbon atoms, a substituted or unsubstituted heteroaryl group having 3 to 60 nuclear carbon atoms, a substituted or unsubstituted alkyl group having 1 to 20 carbon atoms or a substituted or unsubstituted alkoxyl group having 1 to 20 carbon atoms, n represents an integer of 0 to 5, and, when n represents an integer of 2 or greater, the atoms and the groups represented by a plurality of R may be the same with or different from each other, and a plurality of groups represented by R which are adjacent to each other may be bonded to each other to form an aliphatic ring of the carbon ring type or an aromatic ring of the carbon ring type.

Heterocyclic compounds having nitrogen atom represented by the following general formula (C);

$$\text{HAr-L-Ar}^1\text{—Ar}^2 \quad (C)$$

In general formula (C), HAr represents a heterocyclic group having 3 to 40 carbon atoms and nitrogen atom which may have substituents; L represents the single bond or an arylene group having 6 to 60 carbon atoms which may have substituents, a heteroarylene group having 3 to 60 carbon atoms which may have substituents or a fluorenylene group which may have substituents; $Ar^1$ represents a divalent aromatic hydrocarbon group having 6 to 60 carbon atoms which may have substituents; and $Ar^2$ represents an aryl group having 6 to 60 carbon atoms which may have substituents or a heteroaryl group having 3 to 60 carbon atoms which may have substituents.

Silacyclopentadiene derivatives represented by the following general formula (D):

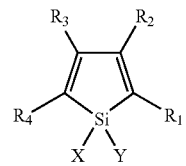

(D)

In general formula (D), X and Y each independently represent a saturated or unsaturated hydrocarbon group having 1 to 6 carbon atoms, an alkoxyl group, an alkenyloxyl group, an alkenyloxyl group, hydroxyl group, a substituted or unsubstituted aryl group, a substituted or unsubstituted heterocyclic group or a saturated or unsaturated cyclic group formed by bonding of the above groups represented by X and Y; and $R_1$ to $R_4$ each independently represent hydrogen atom, a halogen atom, a substituted or unsubstituted alkyl group having 1 to 6 carbon atoms, an alkoxyl group, an aryloxyl group, a perfluoroalkyl group, a perfluoroalkoxyl group, an amino group, an alkylcarbonyl group, an arylcarbonyl group, an alkoxycarbonyl group, an aryloxycarbonyl group, an azo group, an alkylcarbonyloxyl group, an arylcarbonyloxyl group, an alkoxycarbonyloxyl group, an aryloxycarbonyloxyl group, sulfinyl group, sulfonyl group, sulfanyl group, silyl group, carbamoyl group, an aryl group, a heterocyclic group, an alkenyl group, an alkynyl group, nitro group, formyl group, nitroso group, formyloxyl group, isocyano group, cyanate group, isocyanate group, thiocyanate group, isothiocyanate group, a cyano group or, when the groups are adjacent to each other, a structure formed by condensation of substituted or unsubstituted rings.

Borane derivatives represented by the following general formula (E):

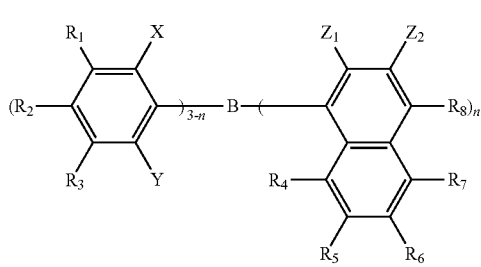

In general formula (E), $R_1$ to $R_8$ and $Z_2$ each independently represent hydrogen atom, a saturated or unsaturated hydrocarbon group, an aromatic hydrocarbon group, a heterocyclic group, a substituted amino group, a substituted boryl group, an alkoxyl group or an aryloxyl group; X, Y and $Z_1$ each independently represent a saturated or unsaturated hydrocarbon group, an aromatic hydrocarbon group, a heterocyclic group, a substituted amino group, an alkoxyl group or an aryloxyl group, and substituents to the groups represented by $Z_1$ and $Z_2$ may be bonded to each other to form a condensed ring; n represents an integer of 1 to 3 and, when n represents an integer of 2 or greater, the plurality of $Z_1$ may represent different groups; and the case where n represents 1, X, Y and $R_2$ each represent methyl group and $R_8$ represents hydrogen atom or a substituted boryl group and the case where n represents 3 and $Z_1$ represents methyl group are excluded.

Compounds represented by general formula (F):

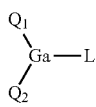

In general formula (F), $Q^1$ and $Q^2$ each independently represent a ligand represented by the following general formula (G):

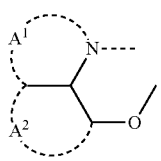

(rings $A^1$ and $A^2$ each representing six-membered aryl cyclic structure which may have substituents and are condensed with each other); and L represents a halogen atom, a substituted or unsubstituted alkyl group, a substituted or unsubstituted cycloalkyl group, a substituted or unsubstituted aryl group, a substituted or unsubstituted heterocyclic group, —$OR^1$ ($R^1$ representing hydrogen atom, a substituted or unsubstituted alkyl group, a substituted or unsubstituted cycloalkyl group, a substituted or unsubstituted aryl group or a substituted or unsubstituted heterocyclic group) or —O—Ga-$Q^3(Q^4)$ ($Q^3$ and $Q^4$ being as defined for $Q^1$ and $Q^2$).

The above metal complex compound strongly exhibits the property as the n-type semiconductor and a great ability of electron injection. Since the energy of formation of the complex compound is small, the bonding between the metal and the ligand in the formed metal complex compound is strong, and the quantum efficiency of fluorescence as the light emitting material is great.

Examples of the substituent to rings $A^1$ ad $A^2$ forming the ligand represented by general formula (G) include halogen atoms such as chlorine atom, bromine atom, iodine atom and fluorine atom; substituted and unsubstituted alkyl groups such as methyl group, ethyl group, propyl group, butyl group, sec-butyl group, tert-butyl group, pentyl group, hexyl group, heptyl group, octyl group, stearyl group and trichloromethyl group; substituted and unsubstituted aryl groups such as phenyl group, naphthyl group, 3-methylphenyl group, 3-methoxyphenyl group, 3-fluorophenyl group, 3-trichloromethylphenyl group, 3-trifluoromethylphenyl group and 3-nitrophenyl group; substituted and unsubstituted alkoxyl groups such as methoxyl group, n-butoxyl group, tert-butoxyl group, trichloromethoxyl group, trifluoroethoxyl group, pentafluoropropoxyl group, 2,2,3,3-tetrafluoropropoxyl group, 1,1,1,3,3,3-hexafluoro-2-propoxyl group and 6-(perfluoroethyl)hexyloxyl group; substituted and unsubstituted aryloxyl groups such as phenoxyl group, p-nitrophenoxyl group, p-tert-butyl-phenoxyl group, 3-fluorophenoxyl group, pentafluorophenoxyl group and 3-trifluorormethylphenoxyl group; substituted and unsubstituted alkylthio groups such as methylthio group, ethylthio group, tert-butylthio group, hexylthio group, octylthio group and trifluoromethylthio group; substituted and unsubstituted arylthio groups such as phenylthio group, p-nitrophenylthio group, p-tert-butylphenylthio group, 3-fluorophenylthio group, pentafluorophenylthio group and 3-trifluoromethylphenylthio group; cyano group; nitro group; amino group; mono- and disubstituted amino groups such as methylamino group, ethylamino group, diethylamino group, dipropylamino group, dibutylamiono group and diphenylamino group; acylamino groups such as bis(acetoxymethyl)amino group, bis(acetoxyethyl)amino group, bis(acetoxypropyl)amino group and bis(acetoxybutyl)amino group; hydroxyl group; siloxyl group; acyl group; carbamoyl groups such as methylcarbamoyl group, dimethylcarbamoyl group, ethylcarbamoyl group, diethylcarbamoyl group, propylcarbamoyl group, butylcarbamoyl group and phenylcarbamoyl group; carboxylic acid group; sulfonic acid group; imide group; cycloalkyl groups such as cyclopentane group and cyclohexyl group; aryl groups such as phenyl group, naphthyl group, biphenyl group, anthranyl group, phenanthryl group, fluorenyl group and pyrenyl group; and heterocyclic groups such as pyridinyl group, pyrazinyl group, pyrimidinyl group, pyridazinyl group, triazinyl group, indolinyl group, quinolinyl group, acridinyl group, pyrrolidinyl group, dioxanyl group, piperidinyl group, morpholidinyl group, piperazinyl group, triatinyl group, carbazolyl group, furanyl group, thiophenyl group, oxazolyl group, oxadiazolyl group, benzoxazolyl group, thiazolyl group, thiadiazolyl group, benzothiazolyl group, triazolyl group, imidazolyl group, benzimidazolyl group and planyl group. The above substituents may be bonded to each other to form a six-membered aryl group or heterocyclic group.

A device comprising a reducing dopant in the interfacial region between a region transporting electrons or the cathode and the organic layer is preferable as an embodiment of the organic EL device of the present invention. The reducing dopant is defined as a substance which can reduce a compound having the electron transporting property. Various compounds can be used as the reducing dopant as long as the compounds have the specific reductive property. For example, at least one substance selected from the group consisting of alkali metals, alkaline earth metals, rare earth metals, oxides of alkali metals, halides of alkali metals, oxides of alkaline earth metals, halides of alkaline earth metals, oxides of rare earth metals, halides of rare earth metals, organic complexes of alkali metals, organic complexes of alkaline earth metals and organic complexes of rare earth metals can be advantageously used.

Preferable examples of the reducing dopant include substances having a work function of 2.9 eV or smaller, specific examples of which include at least one alkali metal selected from the group consisting of Na (the work function: 2.36 eV), K (the work function: 2.28 eV), Rb (the work function: 2.16 eV) and Cs (the work function: 1.95 eV) and at least one alkaline earth metal selected from the group consisting of Ca (the work function: 2.9 eV), Sr (the work function: 2.0 to 2.5 eV) and Ba (the work function: 2.52 eV). Among the above substances, at least one alkali metal selected from the group consisting of K, Rb and Cs is more preferable, Rb and Cs are still more preferable, and Cs is most preferable as the reducing dopant. These alkali metals have great reducing ability, and the luminance of the emitted light and the life of the organic EL device can be increased by addition of a relatively small amount of the alkali metal into the electron injecting zone. As the reducing dopant having a work function of 2.9 eV or smaller, combinations of two or more alkali metals are also preferable. Combinations having Cs such as the combinations of Cs and Na, Cs and K, Cs and Rb and Cs, Na and K are more preferable. The reducing ability can be efficiently exhibited by the combination having Cs. The luminance of emitted light and the life of the organic EL device can be increased by adding the combination having Cs into the electron injecting zone.

In the present invention, an electron injecting layer which is constituted with an insulating material or a semiconductor may be disposed between the cathode and the organic layer. By the electron injecting layer, leak of electric current can be effectively prevented, and the electron injecting property can be improved. As the insulating material, at least one metal compound selected from the group consisting of alkali metal chalcogenides, alkaline earth metal chalcogenides, halides of alkali metals and halides of alkaline earth metals is preferable. It is preferable that the electron injecting layer is constituted with the above substance such as the alkali metal chalcogenide since the electron injecting property can be further improved. Preferable examples of the alkali metal chalcogenide include $Li_2O$, $K_2O$, $Na_2S$, $Na_2Se$ and $Na_2O$. Preferable examples of the alkaline earth metal chalcogenide include CaO, BaO, SrO, BeO, BaS and CaSe. Preferable examples of the halide of an alkali metal include LiF, NaF, KF, LiCl, KCl and NaCl. Preferable examples of the halide of an alkaline earth metal include fluorides such as $CaF_2$, $BaF_2$, $SrF_2$, $MgF_2$ and $BeF_2$ and halides other than the fluorides.

Examples of the semiconductor constituting the electron transporting layer include oxides, nitrides and oxide nitrides of at least one metal selected from Ba, Ca, Sr, Yb, Al, Ga, In, Li, Na, Cd, Mg, Si, Ta, Sb and Zn used singly or in combination of two or more. It is preferable that the inorganic compound constituting the electron transporting layer forms a fine crystalline or amorphous insulating thin film. When the electron injecting layer is constituted with the insulating thin film described above, a more uniform thin film can be formed, and defects of pixels such as dark spots can be decreased. Examples of the inorganic compound include alkali metal chalcogenides, alkaline earth metal chalcogenides, halides of alkali metals and halides of alkaline earth metals which are described above.

(7) Cathode

For the cathode, a material such as a metal, an alloy, a conductive compound or a mixture of these materials which has a small work function (4 eV or smaller) is used as the electrode material to inject electrons into the electron injecting and transporting layer or the light emitting layer. Examples of the electrode material include sodium, sodium-potassium alloys, magnesium, lithium, magnesium-silver alloys, aluminum/aluminum oxide, aluminum-lithium alloys, indium and rare earth metals.

The cathode can be prepared by forming a thin film of the electrode material described above in accordance with a process such as the vapor deposition process and the sputtering process.

When the light emitted from the light emitting layer is obtained through the cathode, it is preferable that the cathode has a transmittance of the emitted light greater than 10%.

It is also preferable that the sheet resistivity of the cathode is several hundred $\Omega/\square$ or smaller. The thickness of the cathode is, in general, selected in the range of 10 nm to 1 μm and preferably in the range of 50 to 200 nm.

(8) Insulating Layer

Defects in pixels tend to be formed in organic EL device due to leak and short circuit since an electric field is applied to ultra-thin films. To prevent the formation of the defects, it is preferable that a layer of a thin film having an insulating property is inserted between the pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide and vanadium oxide. Mixtures and laminates of the above compounds can also be used.

(9) Process for Preparing the Organic EL Device

The organic EL device can be prepared by forming the anode, the light emitting layer, the hole injecting and transporting layer which is formed where necessary, the electron injecting and transporting layer which is formed where necessary, and then the cathode in accordance with the above process using the above materials. The organic EL device may be prepared by forming the above layers in the order reverse to that described above, i.e., the cathode being formed in the first step and the anode in the last step.

An embodiment of the process for preparing an organic EL device having a construction in which an anode, a hole injecting layer, a light emitting layer, an electron injecting layer and a cathode are disposed successively on a substrate transmitting light will be described in the following.

On a suitable substrate which transmits light, a thin film made of a material for the anode is formed in accordance with the vapor deposition process or the sputtering process so that the thickness of the formed thin film is 1 μm or smaller and preferably in the range of 10 to 200 nm. Then, a hole injecting layer is formed on the anode. The hole injecting layer can be formed in accordance with the vacuum vapor deposition process, the spin coating process, the casting process or the LB process, as described above. The vacuum vapor deposition process is preferable since a uniform film can be easily obtained and the possibility of formation of pin holes is small. When the hole injecting layer is formed in accordance with the vacuum vapor deposition process, in general, it is preferable that the conditions are suitably selected in the following ranges: the temperature of the source of the deposition: 50 to 450° C.; the vacuum: $10^{-7}$ to $10^{-3}$ Torr; the rate of deposition: 0.01 to 50 nm/second; the temperature of the substrate: −50 to 300° C.; and the thickness of the film: 5 nm to 5 µm; although the conditions of the vacuum vapor deposition are different depending on the used compound (the material for the hole injecting layer) and the crystal structure and the recombination structure of the hole injecting layer to be formed.

For formation of the light emitting layer on the hole injecting layer formed above, a thin film of the organic light emitting material can be formed using a desired organic light emitting material in accordance with the vacuum vapor deposition process, the sputtering process, the spin coating process or the casting process. The vacuum vapor deposition process is preferable since a uniform film can be easily obtained and the possibility of formation of pin holes is small. When the light emitting layer is formed in accordance with the vacuum vapor deposition process, in general, the conditions of the vacuum vapor deposition process can be selected in the same ranges as those described for the vacuum vapor deposition of the hole injecting layer although the conditions are different depending on the used compound.

The electron injecting layer is formed on the light emitting layer formed above. Similarly to the hole injecting layer and the light emitting layer, it is preferable that the electron injecting layer is formed in accordance with the vacuum vapor deposition process since a uniform film must be obtained. The conditions of the vacuum vapor deposition can be selected in the same ranges as those described for the vacuum vapor deposition of the hole injecting layer and the light emitting layer.

When the vacuum vapor deposition process is used, the aromatic amine derivative of the present invention can be vapor deposited simultaneously with other materials although the process may be different depending on which layer in the light emitting zone and the hole transporting zone comprises the aromatic amine derivative. When the spin coating process is used, the aromatic amine derivative can be used as a mixture with other materials.

The cathode is formed on the electron injecting layer formed above in the last step, and the organic EL device can be obtained.

The cathode is made of a metal and can be formed in accordance with the vacuum vapor deposition process or the sputtering process. It is preferable that the vacuum vapor deposition process is used in order to prevent formation of damages on the lower organic layers during the formation of the film.

In the above preparation of the organic EL device, it is preferable that the above layers from the anode to the cathode are formed successively while the preparation system is kept in a vacuum after being evacuated.

The process for forming the layers in the organic EL device of the present invention is not particularly limited. A conventional process such as the vacuum vapor deposition process and the spin coating process can be used. The organic thin film layer which is used in the organic EL device of the present invention and comprises the compound represented by general formula (1) described above can be formed in accordance with a conventional process such as the vacuum vapor deposition process and the molecular beam epitaxy process (the MBE process) or, using a solution prepared by dissolving the compounds into a solvent, in accordance with a coating process such as the dipping process, the spin coating process, the casting process, the bar coating process and the roll coating process.

The thickness of each layer in the organic thin film layer in the organic EL device of the present invention is not particularly limited. A thickness in the range of several nanometers to 1 µm is preferable since defects such as pin holes tend to be formed when the thickness is excessively small and a great applied voltage is necessary, causing a decrease in the efficiency, when the thickness is excessively great.

When a direct voltage is applied to the organic EL device, emission of light can be observed under application of a voltage of 5 to 40 V in the condition that the anode is connected to a positive electrode (+) and the cathode is connected to a negative electrode (−). When the connection is reversed, no electric current is observed and no light is emitted at all. When an alternating voltage is applied to the organic EL device, the uniform light emission is observed only in the condition that the polarity of the anode is positive and the polarity of the cathode is negative. When an alternating voltage is applied to the organic EL device, any type of wave shape can be used.

EXAMPLES

The present invention will be described more specifically with reference to examples in the following.

Synthesis Example 1

Synthesis of Intermediate Compound 1 and Intermediate Compound 2

Into a three-necked flask, 250 g of m-terphenyl (manufactured by ALDRICH Company), 50 g of hydrogen iodide dihydrate, 75 g of iodine, 750 ml of acetic acid and 25 ml of a concentrated sulfuric acid were placed, and the reaction was allowed to proceed at 70° C. for 3 hours. When the reaction was completed, the reaction mixture was poured into 5 liters of methanol and then stirred for 1 hour, and the resultant mixture was filtered. The obtained crystals were purified in accordance with the column chromatography and recrystallized from acetonitrile, and 17 g of 3'-phenyl-4-iodobiphenyl (Intermediate Compound 1) shown in the following and 17 g of 3-phenyl-5-iodobiphenyl (Intermediate Compound 2) shown in the following were obtained.

Synthesis Example 2

Synthesis of Intermediate Compound 3

Under a stream of argon, 50 g of 2-bromofluorene (manufactured by TOKYO KASEI Co., Ltd.), 100 ml of dimethyl sulfoxide (DMSO), 0.95 g of benzyltriethylammonium chloride (manufactured by HIROSHIMA WAKO Co., Ltd.) and 65 g of a 50% by weight aqueous solution of sodium hydroxide were placed into a 1,000 ml three-necked flask.

The reactor was placed into a water bath, and 44 g of 1,5-dibromo-pentane (manufactured by HIROSHIMA WAKO Co., Ltd.) was added under stirring.

After the reaction was allowed to proceed for 5 hours, 1,000 ml of water was added, and the resultant mixture was treated by extraction with 500 ml of toluene. After the organic layer was dried with magnesium sulfate, the solvent was removed using a rotary evaporator, and 56 g of Intermediate Compound 3 shown in the following was obtained as an oil substance.

Synthesis Example 3

Synthesis of Intermediate Compound 4

The reaction was conducted in accordance with the same procedures as those conducted in Synthesis Example 2 except that 47 g of 1,6-dibromohexane (manufactured by HIROSHIMA WAKO Co., Ltd.) was used in place of 1,5-dibromopentane, and 49 g of Intermediate Compound 4 shown in the following was obtained as an oil substance.

Synthesis Example 4

Synthesis of Intermediate Compound 5

Under a stream of argon, 7.1 g of 2-naphthaleneboronic acid, 12.9 g of 4-iodobromobenzene, 0.6 g of Pd(PPh$_3$)$_4$ (Ph: phenyl group) 60 ml of a 2 M solution of Na$_2$CO$_3$ and 60 ml of dimethoxyethane were placed into a 300 ml three-necked flask, and the resultant mixture was heated at the refluxing temperature for 8 hours. After the reaction mixture was treated by extraction with toluene/water, the organic layer was dried with anhydrous sodium sulfate and concentrated under a reduced pressure. The obtained crude product was purified in accordance with the column chromatography, and 8.0 g of Intermediate Compound 5 shown in the following was obtained as white powder substance.

Synthesis Example 5

Synthesis of Intermediate Compound 6

Under a stream of argon, 35.6 g of Intermediate Compound 1, 80 ml of dehydrated ether and 80 ml of dehydrated toluene were placed into a 500 ml three-necked flask. Then, a hexane solution containing 120 mmole of n-BuLi was added at −30° C., and the reaction was allowed to proceed at 0° C. for 1 hour. The reaction mixture was cooled at −70° C., and 70 ml of B(OiPr)$_3$ (iPr: isopropyl group) was added. The temperature of the obtained mixture was slowly elevated to the room temperature, and the mixture was stirred for 1 hour. After 80 ml of a 10% hydrochloric acid was added, the resultant mixture was treated by extraction with ethyl acetate/water, and the organic layer was dried with anhydrous sodium sulfate. The solution was concentrated and washed with hexane, and 21.4 g of a boronic acid compound was obtained.

Under a stream of argon, 21.4 g of the boronic acid compound obtained above, 18.6 g of 4-iodobromobenzene, 3.8 g of Pd(PPh$_3$)$_4$, 100 ml of a 2 M aqueous solution of Na$_2$CO$_3$ and 160 ml of dimethoxyethane were placed into a 500 ml three-necked flask, and the resultant mixture was heated under the refluxing condition for 8 hours. The reaction fluid was treated by extraction with toluene/water, and the organic layer was dried with anhydrous sodium sulfate. After the dried solution was concentrated under a reduced pressure, the obtained crude product was purified in accordance with the column chromatography, and 15.0 g of Intermediate Compound 6 shown in the following was obtained as a white powder substance.

Synthesis Example 6

Synthesis of Intermediate Compound 7

Under a stream of argon, 5.7 g of benzamide (manufactured by TOKYO KASEI Co., Ltd.), 10 g of 4-bromobiphenyl (manufactured by TOKYO KASEI Co., Ltd.), 0.82 g of copper(I) iodide (manufactured by HIROSHIMA WAKO Co., Ltd.), 0.76 g of N,N'-dimethylethylenediamine (manufactured by ALDRICH Company), 11.8 g of potassium carbonate (manufactured by HIROSHIMA WAKO Co., Ltd.) and 60 ml of xylene were placed into a 200 ml three-necked flask, and the reaction was allowed to proceed at 130° C. for 36 hours.

The reaction mixture was cooled, filtered, washed with toluene, further washed with water and methanol and dried, and 10.5 g of Intermediate Compound 7 shown in the following was obtained as a light yellow powder substance.

Synthesis Example 7

Synthesis of Intermediate Compound 8

The reaction was conducted in accordance with the same procedures as those conducted in Synthesis Example 6 except that 15.2 g of Intermediate Compound 2 was used in place of 10 g of 4-bromobiphenyl, and 16.1 g of Intermediate Compound 8 shown in the following was obtained as a white powder substance.

Synthesis Example 8

Synthesis of Intermediate Compound 9

Under a stream of argon, 21.0 g of Intermediate compound 8, 16.8 g of 4-bromobiphenyl (manufactured by TOKYO KASEI Co., Ltd.), 1.14 g of copper(I) iodide (manufactured by HIROSHIMA WAKO Co., Ltd.), 1.06 g of N,N'-dimethylethylenediamine (manufactured by ALDRICH Company), 20.0 g of potassium carbonate (manufactured by HIROSHIMA WAKO Co., Ltd.) and 100 ml of xylene were placed into a 300 ml three-necked flask, and the reaction was allowed to proceed at 130° C. for 36 hours.

The reaction mixture was cooled, filtered, washed with toluene, further washed with water and methanol and dried, and 14.0 g of a light yellow powder substance was obtained.

Into a 300 ml three-necked flask, 18.0 g of the light yellow powder substance obtained above, 15.1 g of potassium hydroxide (manufactured by HIROSHIMA WAKO Co., Ltd.), 13 ml of ion-exchanged water, 17 ml of xylene (manufactured by HIROSHIMA WAKO Co., Ltd.) and 9 ml of C$_2$H$_5$OH (manufactured by HIROSHIMA WAKO Co., Ltd.) were placed, and the resultant mixture was heated under the refluxing condition for 36 hours. After the reaction was completed, the reaction mixture was treated by extraction with toluene, and the organic layer was dried with magnesium sulfate. The dried solution was concentrated under a reduced pressure, and the obtained crude product was purified in accordance with the column chromatography. The purified product was recrystallized from toluene, separated by filtration and dried, and 9.0 g of Intermediate Compound 9 shown in the following was obtained as a white powder substance.

Synthesis Example 9

Synthesis of Intermediate Compound 10

The reaction was conducted in accordance with the same procedures as those conducted in Synthesis Example 8 except that 25.6 g of Intermediate Compound 1 was used in place of 16.8 g of 4-bromobiphenyl (manufactured by TOKYO KASEI Co., Ltd.), and 8.6 g of Intermediate Compound 10 shown in the following was obtained as a white powder substance.

Synthesis Example 10

Synthesis of Intermediate Compound 11

The reaction was conducted in accordance with the same procedures as those conducted in Synthesis Example 8 except that 22.3 g of 4-bromo-p-terphenyl (manufactured by TOKYO KASEI Co., Ltd.) was used in place of 16.8 g of 4-bromobiphenyl (manufactured by TOKYO KASEI Co., Ltd.), and 8.1 g of Intermediate Compound 11 shown in the following was obtained as a white powder substance.

Synthesis Example 11

Synthesis of Intermediate Compound 12

The reaction was conducted in accordance with the same procedures as those conducted in Synthesis Example 8 except that 21.5 g of Intermediate Compound 3 was used in place of 16.8 g of 4-bromobiphenyl (manufactured by TOKYO KASEI Co., Ltd.), and 10.3 g of Intermediate Compound 12 shown in the following was obtained as a white powder substance.

Synthesis Example 12

Synthesis of Intermediate Compound 13

The reaction was conducted in accordance with the same procedures as those conducted in Synthesis Example 8 except that 22.5 g of Intermediate Compound 4 was used in place of 16.8 g of 4-bromo-biphenyl (manufactured by TOKYO KASEI Co., Ltd.), and 8.2 g of Intermediate Compound 13 shown in the following was obtained as a white powder substance.

Synthesis Example 13

Synthesis of Intermediate Compound 14

The reaction was conducted in accordance with the same procedures as those conducted in Synthesis Example 8 except that 18.0 g of 2-bromo-9,9-dimethylfluorene was used in place of 16.8 g of 4-bromobiphenyl (manufactured by TOKYO KASEI Co., Ltd.), and 10.1 g of Intermediate Compound 14 shown in the following was obtained as a white powder substance.

Synthesis Example 14

Synthesis of Intermediate Compound 15

The reaction was conducted in accordance with the same procedures as those conducted in Synthesis Example 8 except that 20.4 g of Intermediate Compound 5 was used in place of 16.8 g of 4-bromobiphenyl (manufactured by TOKYO KASEI Co., Ltd.), and 7.3 g of Intermediate Compound 15 shown in the following was obtained as a white powder substance.

Synthesis Example 15

Synthesis of Intermediate Compound 16

The reaction was conducted in accordance with the same procedures as those conducted in Synthesis Example 8 except that Intermediate Compound 7 was used in place of Intermediate Compound 8 and 27.7 g of Intermediate Compound 6 was used in place of 16.8 g of 4-bromobiphenyl (manufactured by TOKYO KASEI Co., Ltd.), and 11.2 g of Intermediate Compound 16 shown in the following was obtained as a white powder substance.

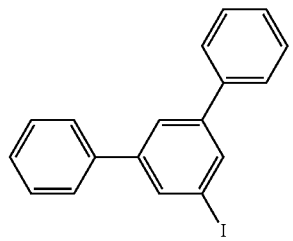

Intermediate Compound 1

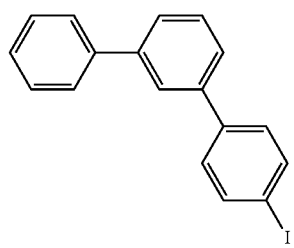

Intermediate Compound 2

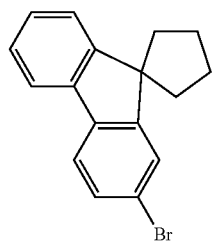

Intermediate Compound 3

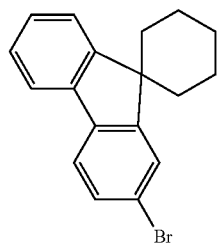

Intermediate Compound 4

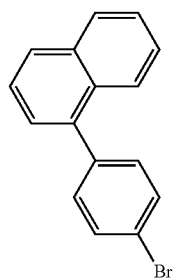

Intermediate Compound 5

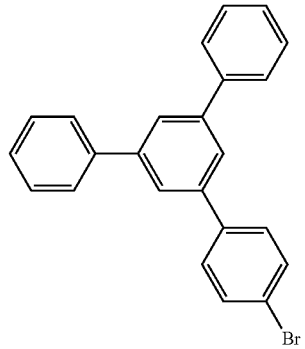

Intermediate Compound 6

Intermediate Compound 7
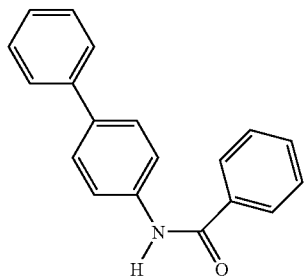
Intermediate Compound 8
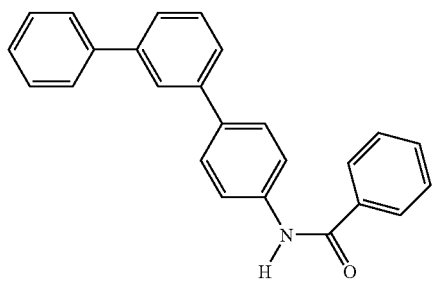
Intermediate Compound 9
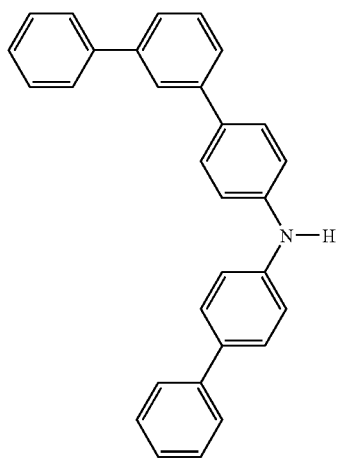
Intermediate Compound 10
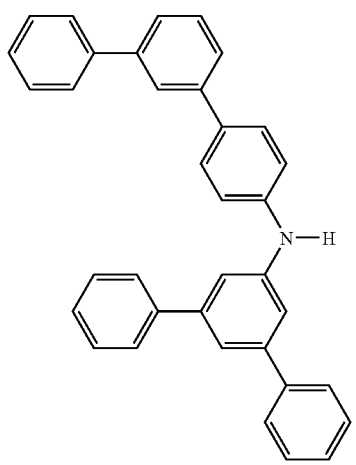
Intermediate Compound 11
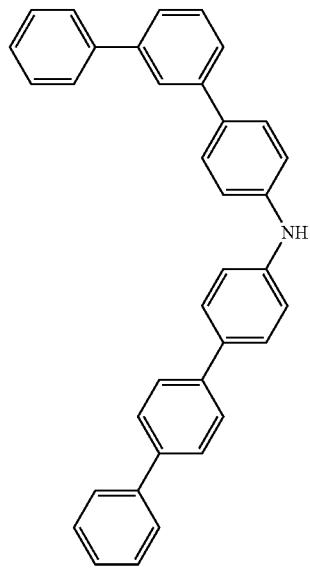
Intermediate Compound 12
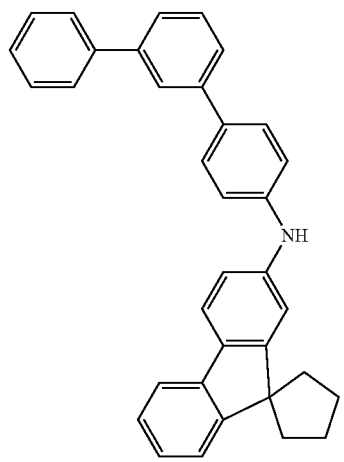
Intermediate Compound 13
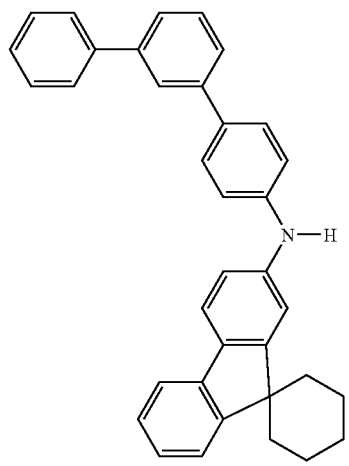

Intermediate Compound 14

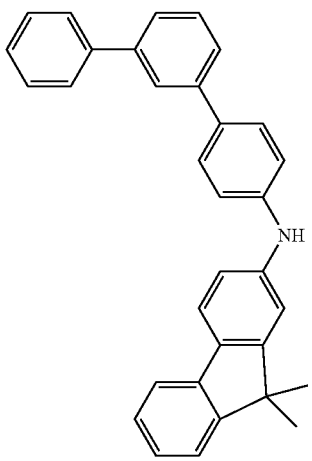

Intermediate Compound 15

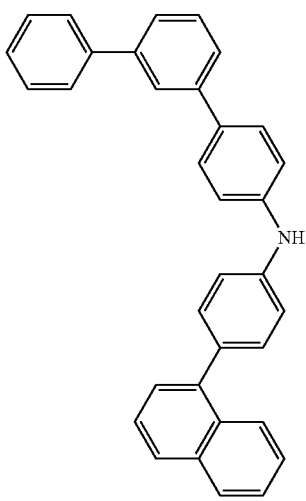

Intermediate Compound 16

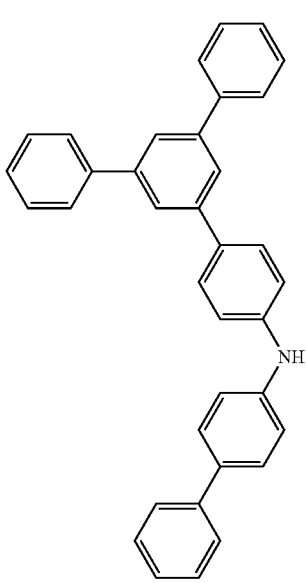

Example of Synthesis 1

Synthesis of Compound H1

Under a stream of argon, 3.2 g of 4,4'-diiodobiphenyl, 7.0 g of Intermediate Compound 9, 4.0 g of t-butoxysodium (manufactured by HIROSHIMA WAKO Co., Ltd.), 0.66 g of bis(triphenylphosphine)-palladium(II) chloride (manufactured by TOKYO KASEI Co., Ltd.) and 300 ml of dehydrated xylene were placed into a reactor, and the reaction was allowed to proceed at 130° C. for 24 hours.

After the reaction mixture was cooled, 500 ml of water was added, and the resultant mixture was filtered through a Celite. The filtrate was treated by extraction, and the organic layer was dried with anhydrous magnesium sulfate and concentrated under a reduced pressure. The obtained crude product was purified in accordance with the column chromatography, recrystallized from toluene, separated by filtration and dried, and 5.8 g of a light yellow powder substance was obtained. In the analysis of FD-MS (a field desorption mass spectrum), the main peak was obtained at m/z=944, which corresponded to $C_{72}H_{52}N_2$=944, and the obtained product was identified to be Compound H1 shown above.

Example of Synthesis 2

Synthesis of Compound H2

The reaction was conducted in accordance with the same procedures as those conducted in Example of Synthesis 1 except that 8.3 g of Intermediate Compound 10 was used in place of Intermediate Compound 9, and 6.5 g of a light yellow powder substance was obtained. In the analysis of FD-MS, the main peak was obtained at m/z=1096, which corresponded to $C_{84}H_{60}N_2$=1096, and the obtained product was identified to be Compound H2 shown above.

Example of Synthesis 3

Synthesis of Compound H3

The reaction was conducted in accordance with the same procedures as those conducted in Example of Synthesis 1 except that 8.3 g of Intermediate Compound 11 was used in place of Intermediate Compound 9, and 7.1 g of a light yellow powder substance was obtained. In the analysis of FD-MS, the main peak was obtained at m/z=1096, which corresponded to $C_{84}H_{60}N_2$=1096, and the obtained product was identified to be Compound H3 shown above.

Example of Synthesis 4

Synthesis of Compound H4

The reaction was conducted in accordance with the same procedures as those conducted in Example of Synthesis 1 except that 7.9 g of Intermediate Compound 12 was used in place of Intermediate Compound 9, and 6.2 g of a light yellow powder substance was obtained. In the analysis of FD-MS, the main peak was obtained at m/z=1076, which corresponded to $C_{82}H_{64}N_2$=1076, and the obtained product was identified to be Compound H4 shown above.

Example of Synthesis 5

Synthesis of Compound H5

The reaction was conducted in accordance with the same procedures as those conducted in Example of Synthesis 1 except that 8.2 g of Intermediate Compound 13 was used in place of Intermediate Compound 9, and 6.8 g of a light yellow powder substance was obtained. In the analysis of FD-MS, the main peak was obtained at m/z=1104, which corresponded to $C_{84}H_{68}N_2=1104$, and the obtained product was identified to be Compound H5 shown above.

Example of Synthesis 6

Synthesis of Compound H6

The reaction was conducted in accordance with the same procedures as those conducted in Example of Synthesis 1 except that 7.7 g of Intermediate Compound 14 was used in place of Intermediate Compound 9, and 5.8 g of a light yellow powder substance was obtained. In the analysis of FD-MS, the main peak was obtained at m/z=1024, which corresponded to $C_{78}H_{60}N_2=1024$, and the obtained product was identified to be Compound H6 shown above.

Example of Synthesis 7

Synthesis of Compound H7

The reaction was conducted in accordance with the same procedures as those conducted in Example of Synthesis 1 except that 7.9 g of Intermediate Compound 15 was used in place of Intermediate Compound 9, and 7.1 g of a light yellow powder substance was obtained. In the analysis of FD-MS, the main peak was obtained at m/z=1044, which corresponded to $C_{80}H_{56}N_2=1044$, and the obtained product was identified to be Compound H7 shown above.

Example of Synthesis 8

Synthesis of Compound H8

The reaction was conducted in accordance with the same procedures as those conducted in Example of Synthesis 1 except that 8.3 g of Intermediate Compound 16 was used in place of Intermediate Compound 9, and 6.4 g of a light yellow powder substance was obtained. In the analysis of FD-MS, the main peak was obtained at m/z=1096, which corresponded to $C_{84}H_{60}N_2=1096$, and the obtained product was identified to be Compound H8 shown above.

Example of Synthesis 9

Synthesis of Compound H9

The reaction was conducted in accordance with the same procedures as those conducted in Example of Synthesis 1 except that 3.1 g of 4,4'-dibromoterphenyl was used in place of 4,4'-diiodobiphenyl, and 6.0 g of a light yellow powder substance was obtained. In the analysis of FD-MS, the main peak was obtained at m/z=1020, which corresponded to $C_{78}H_{56}N_2=1020$, and the obtained product was identified to be Compound H9 shown above.

Example 1

Preparation of an Organic EL Device

A glass substrate (manufactured by GEOMATEC Company) of 25 mm×75 mm×1.1 mm thickness having an ITO transparent electrode was cleaned by application of ultrasonic wave in isopropyl alcohol for 5 minutes and then by exposure to ozone generated by ultraviolet light for 30 minutes.

The cleaned glass substrate having the transparent electrode was attached to a substrate holder of a vacuum vapor deposition apparatus. On the surface of the cleaned substrate at the side having the transparent electrode, a film of H232, which is a compound shown below, having a thickness of 60 nm was formed in a manner such that the formed film covered the transparent electrode. The formed H232 film worked as the hole injecting layer. On the formed H232 film, a film having a thickness of 20 nm of Compound H1 obtained above as the hole transporting material was formed. The formed film worked as the hole transporting layer. On the formed film, EM1, which is a compound shown below, was vapor deposited to form a film having a thickness of 40 nm. At the same time, an amine compound having styryl group D1 shown below as the light emitting molecule was vapor deposited in an amount such that the ratio of the amounts by weight of EM1 to D1 was 40:2. The formed film worked as the light emitting layer.

On the formed film, a film of Alq shown below having a thickness of 10 nm was formed. This film worked as the electron injecting layer. On the film formed above, Li (the source of lithium: manufactured by SAES GETTERS Company) as the reducing dopant and Alq were binary vapor deposited, and an Alq:Li film (the thickness: 10 nm) was formed as the electron injecting layer (the cathode). On the formed Alq:Li film, metallic aluminum was vapor deposited to form a metal cathode, and an organic EL device was prepared.

Using the obtained organic EL device, the efficiency of light emission was measured, and the color of the emitted light was observed. For the measurement of the efficiency of light emission, the luminance was measured using CS1000 manufactured by MINOLTA Co., Ltd., and the efficiency of light emission at 10 mA/cm² was calculated. The half life of light emission was measured at an initial luminance of 5,000 nit at the room temperature under driving with a constant DC current. The results are shown in Table 1.

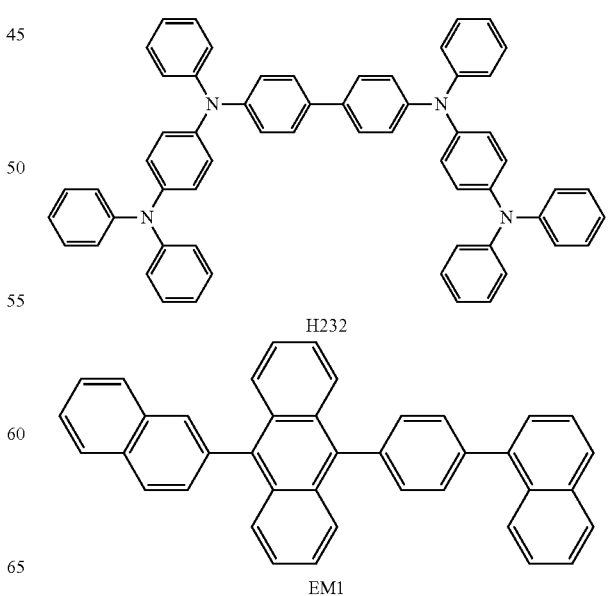

H232

EM1

-continued

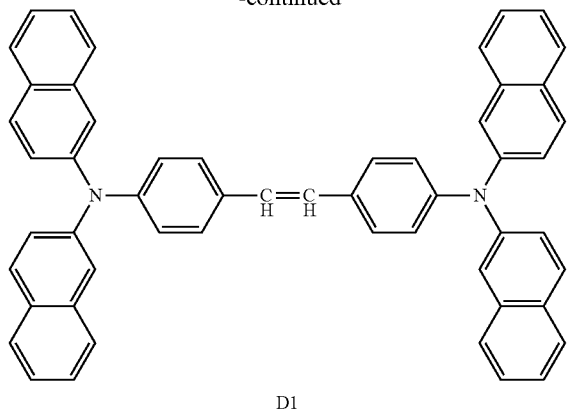

D1

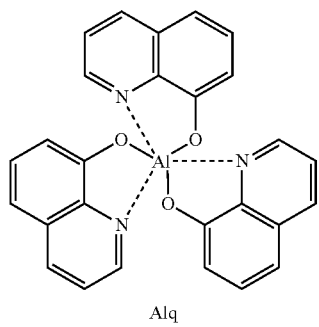

Alq

Examples 2 to 9

Preparation of Organic EL Devices

Organic EL devices were prepared in accordance with the same procedures as those conducted in Example 1 except that compounds shown in Table 1 were used as the hole transporting material in place of Compound H1.

Using the obtained organic EL devices, the efficiency of light emission was measured, and the color of the emitted light was observed. The half life of light emission was measured at an initial luminance of 5,000 nit at the room temperature under driving with a constant DC current. The results are shown in Table 1.

Comparative Examples 1 to 4

Preparation of Organic EL Devices

Organic EL devices were prepared in accordance with the same procedures as those conducted in Example 1 except that Comparative Compound 1 (in Comparative Example 1), Comparative Compound 2 (in Comparative Example 2), Comparative Compound 3 (in Comparative Example 3) and Comparative Compound 4 (in Comparative Example 4) were used as the hole transporting material in place of Compound H1. Comparative Compound 3 and Comparative Compound 4 were crystallized during the vapor deposition, and normal organic EL devices could not be prepared.

Using the obtained organic EL devices, the efficiency of light emission was measured, and the color of the emitted light was observed. The half life of light emission was measured at an initial luminance of 5,000 nit at the room temperature under driving with a constant DC current. The results are shown in Table 1.

TABLE 1

|  | Hole transporting material | Efficiency of light emission (cd/A) | Color of emitted light | Half life (hour) |
| --- | --- | --- | --- | --- |
| Example 1 | H1 | 5.1 | blue | 460 |
| Example 2 | H2 | 4.8 | blue | 390 |
| Example 3 | H3 | 5.4 | blue | 420 |
| Example 4 | H4 | 5.0 | blue | 370 |
| Example 5 | H5 | 4.9 | blue | 350 |
| Example 6 | H6 | 5.0 | blue | 370 |
| Example 7 | H7 | 5.1 | blue | 430 |
| Example 8 | H8 | 5.2 | blue | 420 |
| Example 9 | H9 | 4.9 | blue | 340 |
| Comparative Example 1 | Comparative Compound 1 | 5.1 | blue | 250 |
| Comparative Example 2 | Comparative Compound 2 | 5.0 | blue | 290 |
| Comparative Example 3 | Comparative Compound 3 | 5.1 | blue | 270 |
| Comparative Example 4 | Comparative Compound 4 | 4.9 | blue | 220 |

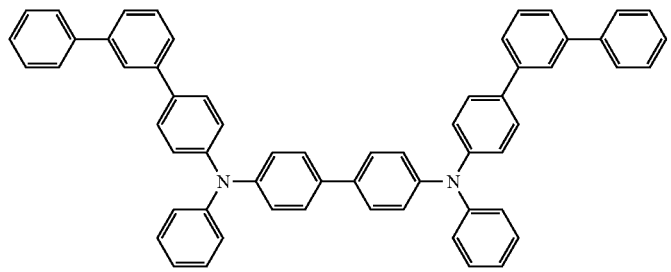

Comparative Compound 1

TABLE 1-continued
| Hole transporting material | Efficiency of light emission (cd/A) | Color of emitted light | Half life (hour) |
| --- | --- | --- | --- |
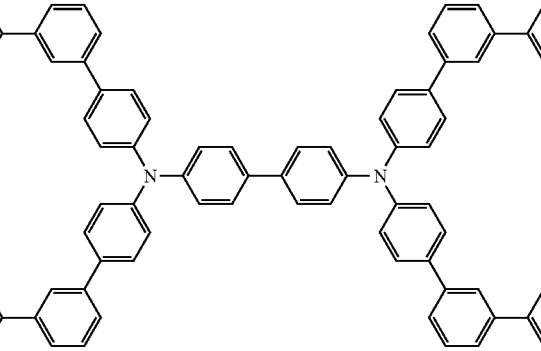
Comparative Compound 2
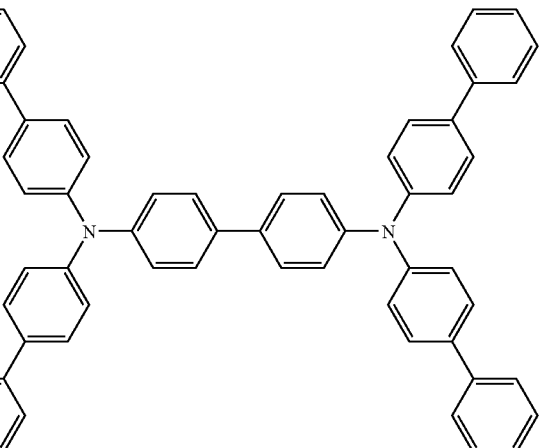
Comparative Compound 3
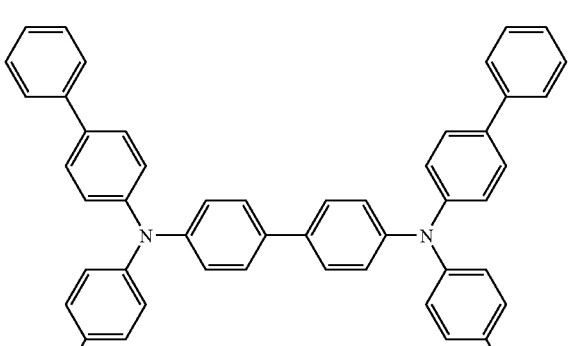
Comparative Compound 4

Example 10

Preparation of an Organic EL Device

An organic EL device was prepared in accordance with the same procedures as those conducted in Example 1 except that an arylamine compound D2 shown below was used in place of the amine compound having styryl group D1. Me represents methyl group.

Using the obtained organic EL device, the efficiency of light emission was measured and found to be 5.2 cd/A. The color of the emitted light was blue. The half life of light emission was measured at an initial luminance of 5,000 nit at the room temperature under driving with a constant DC current and found to be 430 hours.

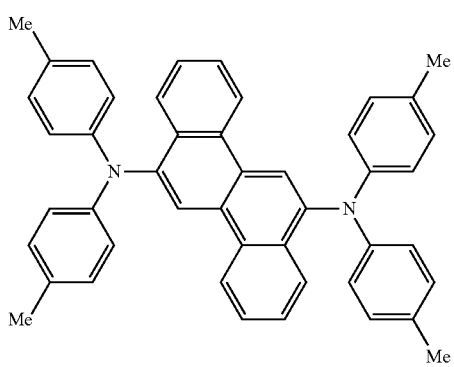

D2

Comparative Example 5

An organic EL device was prepared in accordance with the same procedures as those conducted in Example 10 except that Comparative Compound 1 shown above was used as the hole transporting material in place of Compound H1.

Using the obtained organic EL device, the efficiency of light emission was measured and found to be 4.9 cd/A. The color of the emitted light was blue. The half life of light emission was measured at an initial luminance of 5,000 nit at the room temperature under driving with a constant DC current and found to be 270 hours.

As the above results show, when the aromatic amine derivative of the present invention was used as the hole transporting material of an organic EL device, the light emission could be achieved at the same efficiency of light emission as that of devices using a conventional material, and no crystallization took place during the vapor deposition. Therefore, the aromatic amine derivative of the present invention was very effective for increasing the life of the device.

INDUSTRIAL APPLICABILITY

As described specifically in the above, crystallization of the aromatic amine derivative of the present invention is suppressed since the interaction between the molecules is small due to the great steric hindrance. Therefore, the yield in the production of the organic EL device is increased, and the organic EL device having a long life in combination with a sustained great efficiency of light emission can be obtained.

The invention claimed is:

1. An aromatic amine derivative represented by following general formula (1):

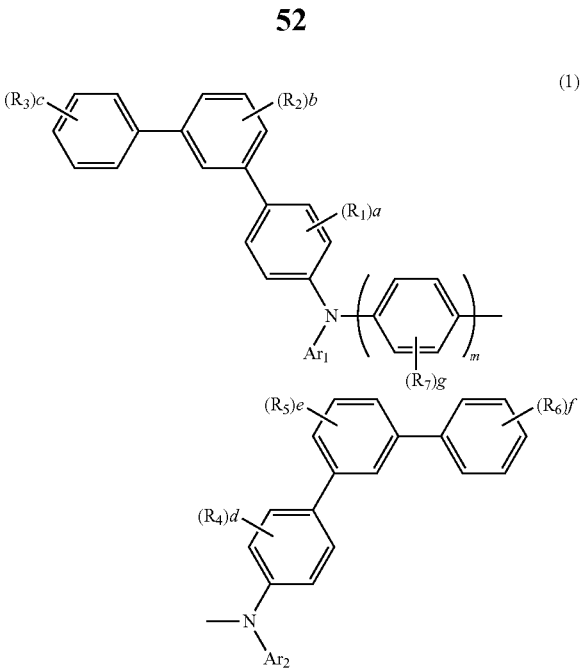

wherein $R_1$ to $R_6$ each independently represent a substituted or unsubstituted alkyl group having 1 to 10 carbon atoms, a substituted or unsubstituted alkoxyl group having 1 to 10 carbon atoms or a substituted or unsubstituted phenyl group, $R_7$ represents a substituted or unsubstituted alkyl group having 1 to 10 carbon atoms or a substituted or unsubstituted alkoxyl group having 1 to 10 carbon atoms, a, b, d, e and g each represent an integer of 0 to 4, c and f each represent an integer of 0 to 5, and m represents an integer of 1 to 3; and $Ar_1$ and $Ar_2$ both represent p-biphenyl group or $Ar_1$ and $Ar_2$ each represent a group represented by following general formula (2), (3) or (4):

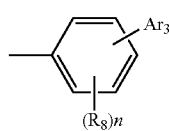

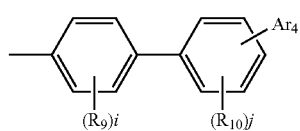

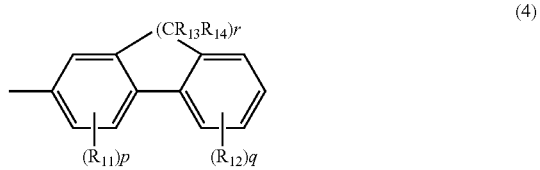

in general formula (2), $R_8$ representing a substituted or unsubstituted alkyl group having 1 to 10 carbon atoms, a substituted or unsubstituted alkoxyl group having 1 to 10 carbon atoms or a substituted or unsubstituted phenyl group, $Ar_3$ representing a substituted or unsubstituted α-naphthyl group bonded to p-position or $Ar_3$ representing a substituted or unsubstituted phenyl group, a substituted or unsubstituted α-naphthyl group, a substituted or unsubstituted β-naphthyl group or a substituted or unsubstituted ortho-(o-), meta-(m-) or para-(p-)biphenyl group, each bonded to o- or m-position, and n representing an integer of 0 to 4;

in general formula (3), $R_9$ and $R_{10}$ each independently representing a substituted or unsubstituted alkyl group having 1 to 10 carbon atoms, a substituted or unsubstituted alkoxyl group having 1 to 10 carbon atoms or a substituted or unsubstituted phenyl group, $Ar_4$ representing a substituted or unsubstituted phenyl group, bonding position of the group represented by $Ar_4$ being o- or p-position, and i and j each representing an integer of 0 to 4; and in general formula (4), $R_{11}$ and $R_{12}$ each independently representing a substituted or unsubstituted alkyl group having 1 to 10 carbon atoms, a substituted or unsubstituted alkoxyl group having 1 to 10 carbon atoms or a substituted or unsubstituted phenyl group, p representing an integer of 0 to 3, q representing an integer of 0 to 4, $R_{13}$ and $R_{14}$ each independently representing single bond, hydrogen atom, a substituted or unsubstituted alkyl group having 1 to 6 carbon atoms or a group represented by following general formula (5), and r representing an integer of 1 or 2;

$$-(CR_{15}R_{16})_s- \quad (5)$$

in general formula (5), $R_{15}$ and $R_{16}$ each independently representing hydrogen atom or a substituted or unsubstituted alkyl group having 1 to 6 carbon atoms, and s representing an integer of 3 to 6.

2. An aromatic amine derivative according to claim 1, wherein numbers of nuclear carbon atoms in the groups represented by $Ar_1$ and $Ar_2$ in general formula (1) are each independently 7 to 17.

3. An aromatic amine derivative according to claim 1, wherein $Ar_1$ and $Ar_2$ in general formula (1) both represent p-biphenyl group.

4. An aromatic amine derivative according to claim 1, wherein, in general formula (1), b and e both represent 1, and $R_2$ and $R_5$ both represent phenyl group.

5. An aromatic amine derivative according to claim 1, wherein, in general formula (1), b and e both represent 1, and $R_2$ and $R_5$ both represent phenyl group having bonding position at m-position thereof.

6. An aromatic amine derivative according to claim 1, wherein $Ar_3$ in general formula (2) represents a substituted or unsubstituted α-naphthyl group or a substituted or unsubstituted α-naphthyl group.

7. An aromatic amine derivative according to claim 1, wherein $Ar_3$ in general formula (2) represents a substituted or unsubstituted α-naphthyl group, and bonding position thereof is p-position.

8. An aromatic amine derivative according to claim 1, wherein, in general formula (2), bonding position of the group represented by $Ar_3$ is m-position, n represents 1, and $R_8$ represents phenyl group, bonding position thereof being m-position.

9. An aromatic amine derivative according to claim 1, wherein bonding position of the group represented by $Ar_4$ in general formula (3) is p-position.

10. An aromatic amine derivative according to claim 1, wherein r in general formula (4) represents 1.

11. An aromatic amine derivative according to claim 1, which is a material for organic electroluminescence devices.

12. An aromatic amine derivative according to claim 1, which is a hole transporting material for organic electroluminescence devices.

13. An organic electroluminescence device comprising a cathode, an anode and an organic thin film layer which is disposed between the cathode and the anode and comprises at least one layer comprising at least a light emitting layer, wherein at least one layer in the organic thin film layer comprises an aromatic amine derivative described in claim 1 singly or as a component of a mixture.

14. An organic electroluminescence device according to claim 13, wherein the organic thin film layer comprises a hole transporting layer, and the hole transporting layer comprises an aromatic amine derivative described in claim 1 singly or as a component of a mixture.

15. An organic electroluminescence device according to claim 13, wherein the light emitting layer comprises an arylamine compound and/or a styrylamine compound.

16. An organic electroluminescence device according to claim 13, which emits blue light.

* * * * *